(12) United States Patent
Kazama et al.

(10) Patent No.: US 11,505,816 B2
(45) Date of Patent: Nov. 22, 2022

(54) **MEDIUM FOR DETECTING *STAPHYLOCOCCUS AUREUS*, SHEET FOR DETECTING *S. AUREUS* COMPRISING SAME, AND METHOD FOR DETECTING *S. AUREUS* USING SAME**

(71) Applicant: DAI NIPPON PRINTING CO., LTD., Tokyo (JP)

(72) Inventors: Keisuke Kazama, Tokyo (JP); Rui Saitou, Tokyo (JP)

(73) Assignee: KIKKOMAN CORPORATION, Chiba (JP)

( * ) Notice: Subject to any disclaimer, the term of this patent is extended or adjusted under 35 U.S.C. 154(b) by 92 days.

(21) Appl. No.: 17/031,250

(22) Filed: Sep. 24, 2020

(65) Prior Publication Data

US 2021/0017566 A1    Jan. 21, 2021

Related U.S. Application Data

(62) Division of application No. 16/071,037, filed as application No. PCT/JP2017/002629 on Jan. 26, 2017, now Pat. No. 10,822,632.

(30) Foreign Application Priority Data

Jan. 29, 2016  (JP) .................................. 2016-016378
Jun. 7, 2016   (JP) .................................. 2016-113278

(51) Int. Cl.
*C12Q 1/04*      (2006.01)
*C12N 1/20*      (2006.01)
(Continued)

(52) U.S. Cl.
CPC ............... *C12Q 1/045* (2013.01); *C12N 1/20* (2013.01); *C12N 1/205* (2021.05); *C12Q 1/14* (2013.01);
(Continued)

(58) Field of Classification Search
CPC . C12Q 1/045; C12Q 1/14; C12Q 1/34; C12Q 1/42; C12N 1/20; C12N 1/205; C12R 1/445; C12R 2001/445; C12M 1/34
See application file for complete search history.

(56) References Cited

U.S. PATENT DOCUMENTS

| 4,814,276 A | 3/1989 | Evans et al. |
| 2011/0039288 A1 | 2/2011 | Roche et al. |
| 2012/0107913 A1 | 5/2012 | Baba et al. |

FOREIGN PATENT DOCUMENTS

| CN | 1518602 | 8/2004 |
| CN | 102471747 | 5/2012 |

(Continued)

OTHER PUBLICATIONS

International Search Report issued in International Application No. PCT/JP2017/002629 dated Apr. 4, 2017 (5 pages).
(Continued)

*Primary Examiner* — Louise W Humphrey
*Assistant Examiner* — Anjali Ajit Hirani
(74) *Attorney, Agent, or Firm* — Hamre, Schumann, Mueller & Larson, P.C.

(57) ABSTRACT

The purpose of the present invention is to provide a detection means whereby *Staphylococcus aureus* can be identified at a high accuracy. An aspect of the present invention relates to a medium for detecting *S. aureus* which comprises one or more kinds of nutrient components, a color developing agent capable of developing a color in the presence of α-glucosidase, a color developing agent capable of developing a color in the presence of phosphatase and 0.5 mg/cm³ or more of sodium colistin methanesulfonate. Another aspect of the present invention relates to a sheet for detecting *S. aureus*, said sheet comprising the aforesaid medium, and a method for detecting *S. aureus* with the use of the medium and sheet as described above.

15 Claims, 11 Drawing Sheets

(51) Int. Cl.
*C12M 1/34* (2006.01)
*C12Q 1/14* (2006.01)
*C12Q 1/42* (2006.01)
*C12Q 1/34* (2006.01)
*C12R 1/445* (2006.01)

(52) U.S. Cl.
CPC .............. *C12Q 1/34* (2013.01); *C12Q 1/42* (2013.01); *C12M 1/34* (2013.01); *C12R 2001/445* (2021.05)

(56) References Cited

FOREIGN PATENT DOCUMENTS

| EP | 1 165 831 | 1/2002 |
|---|---|---|
| JP | 09-508279 | 8/1997 |
| JP | 2004-524041 | 8/2004 |
| WO | 9520674 | 8/1995 |
| WO | 02079486 | 10/2002 |
| WO | 2011007802 | 1/2011 |

OTHER PUBLICATIONS

Written Opinion issued in International Application No. PCT/JP2017/002629 dated Apr. 4, 2017 (4 pages).

(a)

(b)

(c)

(a)

(b)

(c)

(a)  (d)

(b)  (e)

(c)  (f)

(a)

(d)

(b)

(e)

(c)

(f)

(a)

(d)

(b)

(e)

(c)

(f)

(a) 
(d) 
(b) 
(e) 
(c) 
(f)

(a)

(d)

(b)

(e)

(c)

(f)

MEDIUM FOR DETECTING STAPHYLOCOCCUS AUREUS, SHEET FOR DETECTING S. AUREUS COMPRISING SAME, AND METHOD FOR DETECTING S. AUREUS USING SAME

TECHNICAL FIELD

The present invention relates to a medium used for detecting Staphylococcus aureus, a sheet used for detecting S. aureus comprising such medium, and a method for detecting S. aureus using such medium and such sheet.

BACKGROUND ART

S. aureus is a type of bacteria that produces various toxins. Also, S. aureus is a pathogenic bacterium of septicemia, endocarditis, and serious bacterial infections, such as an infection of the lung or osteoarthritis. Accordingly, a means capable of detecting S. aureus in a simple manner with high accuracy has been desired at, for example, facilities that handle food or beverage products (e.g., factories and restaurants) and medical institutions.

For example, Patent Literature 1 discloses a method of identifying and enumerating staphylococci in a sample containing one or more types of bacteria, which is characterized by: the steps of i) inoculating a selective medium with an aliquot of a sample, wherein the medium comprises inhibitors to promote the growth of staphylococci, a first substrate capable of producing an observable first color in the presence of β-glucosidase, and second substrate capable of producing a second color in the presence of staphylococci; ii) incubating the inoculated medium to produce the bacterial colony of sufficient size to allow visualization of the bacterial colony in the presence of the first and second substrates in the medium; and iii) enumerating the colony identified by the presence of the second color of the second substrate to give the number of staphylococci in the sample. This literature describes that the inhibitors can be selected from the group consisting of colistin methanesulfonate, nalidixic acid, and lithium chloride. This literature also describes that the first substrate is an indolyl-glucopyranoside substrate providing a visual color change in the presence of β-glucosidase and the second substrate provides a visual color change in the presence of *staphylococcus*.

Patent Literature 2 discloses a medium for the detection of S. aureus and/or coagulase-positive Staphylococci, which comprises a S. aureus culture medium and at least one enzyme substrate for demonstrating α-glucosidase activity. This literature describes an indoxyl-based compound as at least one enzyme substrate for demonstrating α-glucosidase activity.

In general, the medium and the culture medium disclosed in Patent Literatures 1 and 2 are used in the form of a plane solid medium formed in a sterile petri dish with the use of a gelling agent such as agar. In such a case, occasionally, sophisticated techniques are required for preparation of a plane solid medium, fractionation of samples, culture of microorganisms, and other procedures.

Patent Literature 3 discloses a microorganism culture sheet having a base sheet, a culture layer formed on top of the base sheet, and a cover sheet that covers the culture layer, wherein the culture layer is pattern-formed with a medium liquid comprising polyvinylpyrrolidone and at least one member selected from the group consisting of a gelling agent, a nutrient component, a color indicator, a selective agent, and a substrate. This literature describes that cell count testing and the like of food or beverage products can be performed in a simple and stable manner with the use of the microorganism culture sheet.

CITATION LIST

Patent Literature

Patent Literature 1: JP H09-508279 A (1997)
Patent Literature 2: JP 2004-524041 A
Patent Literature 3: International Publication WO 2011/007802

SUMMARY OF INVENTION

Technical Problem

To date, several means for detecting S. aureus have been known, although these known means remain improvable. When the medium described in Patent Literature 1 or 2 is applied to a particular embodiment, for example, staphylococcal bacteria other than S. aureus may be detected as false-positive strains.

Accordingly, the present invention is intended to provide a means of detection that enables identification of S. aureus with high accuracy.

Solution to Problem

The present inventors have examined the means described above in various ways. The present inventors added a color developing substrate specific to two types of enzymes expressed in S. aureus and a highly concentrated selection agent to a medium and found that S. aureus could be detected with high accuracy on the basis of the color of the colony formed on the medium as an indicator. The present invention has been completed on the basis of such finding.

Specifically, the present invention is summarized as follows.

(1) A medium used for detecting Staphylococcus aureus comprising one or more nutrient components, a color developer that develops color in the presence of α-glucosidase, a color developer that develops color in the presence of phosphatase, and colistin sodium methanesulfonate at 0.5 mg/cm$^3$ or more.
(2) The medium according to (1), wherein the color developer that develops color in the presence of α-glucosidase is 6-chloro-3-indoxyl-α-D-glucoside, and the color developer that develops color in the presence of phosphatase is 5-bromo-3-indoxyl phosphate.
(3) The medium according to (1), wherein the color developer that develops color in the presence of α-glucosidase is 5-bromo-4-chloro-3-indoxyl-α-D-glucoside, and the color developer that develops color in the presence of phosphatase is 5-bromo-6-chloro-3-indoxyl phosphate.
(4) The medium according to any of (1) to (3), which comprises colistin sodium methanesulfonate at 0.5 to 4.1 mg/cm$^3$.
(5) The medium according to (4), which comprises colistin sodium methanesulfonate at 0.5 to 2.8 mg/cm$^3$.
(6) The medium according to (5), which comprises colistin sodium methanesulfonate at 2.3 to 2.8 mg/cm$^3$.
(7) A microorganism culture substrate used for detection of Staphylococcus aureus comprising a substrate and a culture layer provided on an upper surface of the substrate, wherein the culture layer comprises the medium according to any of (1) to (6).

(8) The microorganism culture substrate according to (7), which further comprises the substrate in the form of a sheet and a cover sheet covering the culture layer, wherein the culture layer further comprises polyvinylpyrrolidone and one or more gelling agents.

(9) A method for detecting *Staphylococcus aureus* comprising:

a step of sample addition comprising adding a microorganism-containing sample to the medium according to any of (1) to (6) or the culture layer of the microorganism culture substrate according to (7) or (8);

a step of colony formation comprising incubating the medium or microorganism culture substrate added with the sample to form a microbial colony; and a step of strain identification comprising identifying *Staphylococcus aureus* on the basis of the color of the resulting microbial colony.

(10) The method according to (9), wherein the step of sample addition comprises adding the microorganism-containing sample to the culture layer of the microorganism culture substrate according to (7) or (8), and the culture layer of the microorganism culture substrate comprises colistin sodium methanesulfonate at 0.2 mg/ml or more relative to the total volume of the microorganism-containing sample.

Advantageous Effects of Invention

The present invention can provide a means of detection that enables identification of *S. aureus* with high accuracy.

DESCRIPTION OF EMBODIMENTS

Figure 1:
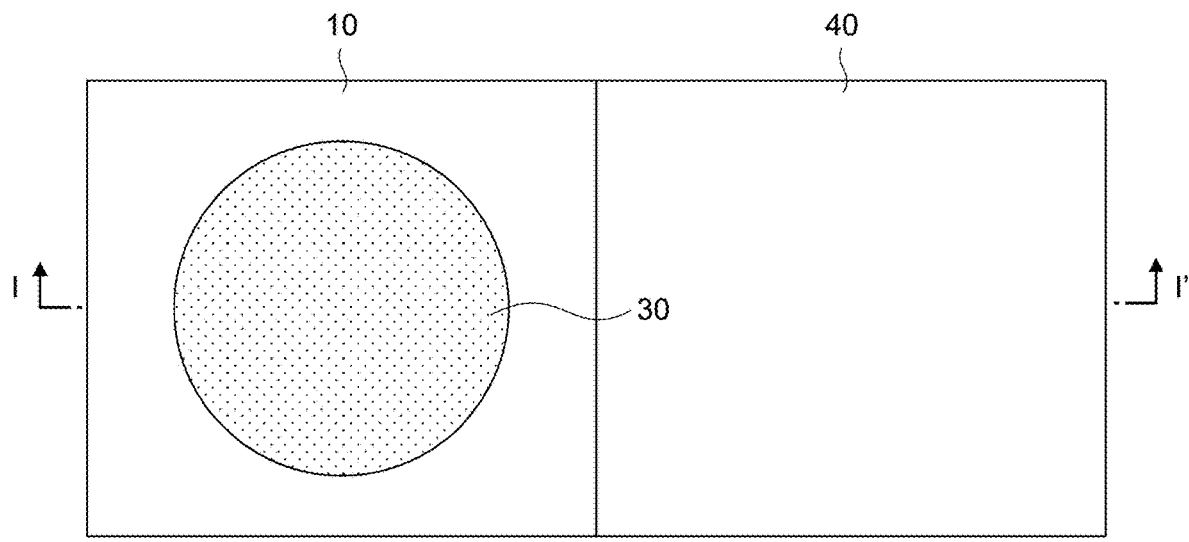
FIG. 1 shows an embodiment of the microorganism culture substrate used for detecting *S. aureus* according to an aspect of the present invention; (a): a top view of the microorganism culture substrate according to an aspect of the present invention; (b): a schematic side cross sectional view taken along I-I' in (a); and (c): a schematic side cross sectional view showing a culture layer covered with a folded cover sheet.
Figure 1:
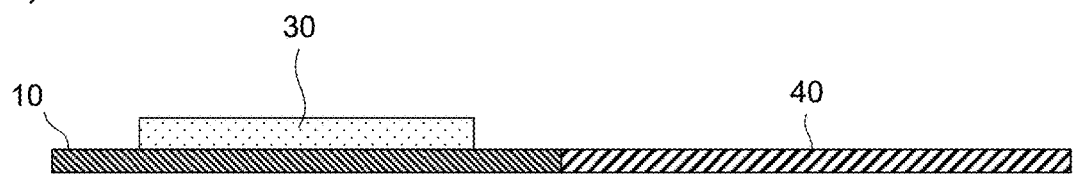
Figure 1:
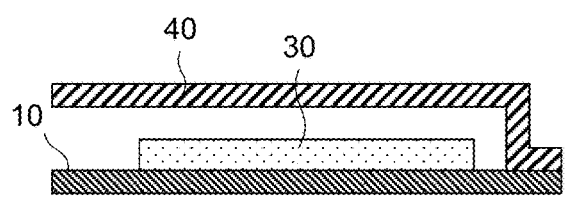

The features of the present invention are described with reference to adequate figures herein. In the figures, dimensions and configurations of components are exaggerated for clarification, so that actual dimensions and configurations are not accurately demonstrated. Accordingly, the technical scope of the present invention is not limited to the dimensions and the configurations of the components demonstrated in the figures.

<1: Medium for Detecting *Staphylococcus aureus*>

An aspect of the present invention relates to a medium used for detecting *Staphylococcus aureus*.

In the present invention, the term "*Staphylococcus aureus*" refers to *Staphylococcus aureus*. *S. aureus* is a Gram-positive bacterium of the genus *Staphylococcus*. In general, the presence of *S. aureus* can be confirmed by conducting a culture test using a *S. aureus* selection medium, such as a Baird-Parker agar medium or a mannitol salt agar medium supplemented with egg yolk. A culture test involving the use of such selection medium comprises allowing *S. aureus* to selectively grow with the aid of a selection agent added to the medium and identifying *S. aureus* on the basis of, for example, egg yolk reactivity or mannitol degradability. A culture test involving the use of such selection medium, however, may occasionally detect staphylococcal bacteria other than *S. aureus* as false-positive strains. In general, accordingly, an additional coagulase test using coagulase activity as an indicator is performed after the culture test, so as to identify *S. aureus*. Coagulase is an exoenzyme having activity of plasma clotting, which is expressed in *S. aureus*. Coagulase is known to be associated with human pathogenicity caused by *S. aureus*. Accordingly, it was believed that with the use of coagulase activity as an indicator staphylococcal bacteria of interest can be detected separately from non-staphylococcal bacteria, such as *Enterococcus* and spore-forming *Bacillus* bacteria, and many staphylococcal bacteria other than *S. aureus*. However, several staphylococcal bacteria other than *S. aureus* have the coagulase-producing ability as with *S. aureus*. Therefore, such staphylococcal bacteria may be detected as false-positive strains in the test for detecting S. aureus using coagulase activity as an indicator.

Accordingly, means for detecting S. aureus using activity of enzymes other than coagulase, such as various exoenzymes, including α-glucosidase, phosphatase, β-glucuronidase, β-galactosidase, and β-glucosidase, were developed (e.g., Patent Literature 1 and Patent Literature 2). With such detection means, however, staphylococcal bacteria other than S. aureus may occasionally be detected as false-positive strains because of factors, such as a combination of enzymes to be used together and/or culture conditions.

When α-glucosidase is used in combination with phosphatase, for example, it was considered that S. aureus would be expressed in response to both the aforementioned enzymes as exoenzyme while staphylococcal bacteria other than S. aureus would be expressed in response to either one or neither of the enzymes. Accordingly, it was considered that S. aureus could be specifically detected with the use of activities of two types of the enzymes, i.e., α-glucosidase and phosphatase, as indicators (Patent Literature 2). However, the present inventors have found that several staphylococcal bacteria other than S. aureus could occasionally be detected as false-positive strains by the test using activities of two types of the enzymes, α-glucosidase and phosphatase as indicators.

The present inventors have found that S. aureus could be detected with high accuracy on the basis of the color of the colony formed on a medium as the indicators with the addition of a highly-concentrated selection agent to the medium, in addition to two types of color developing substrates specific to exoenzymes other than coagulase expressed in S. aureus; i.e., α-glucosidase and phosphatase.

The medium used for detecting S. aureus according to the present aspect is required to comprise one or more nutrient components, a color developer that develops color in the presence of α-glucosidase, a color developer that develops color in the presence of phosphatase, and colistin sodium methanesulfonate at high concentration. With the use of the medium according to the present aspect that comprises colistin sodium methanesulfonate at high concentration in addition to the two types of color developing substrates, S. aureus can be selectively detected with high accuracy without detecting staphylococcal bacteria other than S. aureus as false-positive strains, as well as microorganisms other than those of staphylococcal bacteria.

One or more nutrient components to be used in the medium according to the present aspect can be adequately selected from among substances that are generally used in the art as nutrient components for media used for detection of S. aureus. Examples of nutrient components include, but are not limited to: peptone, tryptone, soytone, meat extract, yeast extract, sodium pyruvate, and an egg yolk mixture; sugar or sugar alcohol, such as D(-)-mannitol; inorganic salts, such as potassium phosphate, sodium phosphate, sodium carbonate, and potassium carbonate; and amino acids, such as glycine. A person skilled in the art can adequately determine the concentration of the nutrient components within the range that is generally adopted in the art on the basis of, for example, the condition of the medium according to the present aspect and/or the sample containing the target microorganisms at the time of use, the volume thereof, and/or the culture condition.

In the present invention, the term "selection agent" refers to a compound having antibacterial activity of suppressing the growth of particular types of microorganisms other than the target of detection; i.e., S. aureus. In this description, a compound having antibacterial activity is occasionally referred to as an "antibacterial agent." The medium according to the present aspect comprises, as a selection agent, colistin sodium methanesulfonate at 0.5 mg/cm$^3$ or more. The concentration of colistin sodium methanesulfonate is preferably 0.5 to 4.1 mg/cm$^3$, more preferably 0.5 to 2.8 mg/cm$^3$, further preferably 2.3 to 2.8 mg/cm$^3$, and particularly preferably about 2.5 mg/cm$^3$. Such concentration is defined as mass concentration relative to the total volume of the medium according to the present aspect. When an aspect of the present invention concerns a microorganism culture substrate used for detecting S. aureus comprising a substrate and a culture layer containing the medium according to the present aspect provided on the upper surface of the substrate, for example, such concentration is defined as mass concentration relative to the total volume of the dried culture layer of the medium according to the present aspect. In such a case, the mass concentration of colistin sodium methanesulfonate relative to the total volume of a sample to be added to the dried culture layer is generally 0.2 mg/ml or more, preferably 0.2 to 1.6 mg/ml, more preferably 0.2 to 1.1 mg/ml, further preferably 0.9 to 1.1 mg/ml, and particularly preferably about 1 mg/ml. Colistin sodium methanesulfonate is a compound known as an antibacterial agent against Gram-negative bacteria. It is generally used at a concentration of 0.1 mg/ml (100 μg/ml) or lower, such as 1 to 20 μg/ml (Japanese Journal of Chemotherapy, Vol. 60, No. 4, pp. 446-467, 2012). In general, colistin sodium methanesulfonate is not used as an antibacterial agent against Gram-positive bacteria such as staphylococci. The present inventors have discovered that colistin sodium methanesulfonate would exert the growth inhibitory activity at high concentration of 0.5 mg/cm$^3$ or higher on staphylococcal bacteria other than S. aureus (i.e., S. saprophyticus subsp. saprophyticus), 1.3 mg/cm$^3$ or higher on S. carnosus, and 2.3 mg/cm$^3$ or higher on S. xylosus and S. sciuri. When the concentration of colistin sodium methanesulfonate is 0.5 mg/cm$^3$ (0.2 mg/ml in terms of mass concentration relative to the total volume of a sample added to the dried culture layer in the aspect of the microorganism culture substrate) or higher, accordingly, the growth of S. saprophyticus subsp. saprophyticus can be substantially suppressed, and detection of such strain as a false-positive strain can be prevented. When the concentration of colistin sodium methanesulfonate is 2.3 mg/cm$^3$ (0.9 mg/ml in terms of mass concentration relative to the total volume of a sample to be added to the dried culture layer in the aspect of the microorganism culture substrate) or higher, in addition to S. saprophyticus subsp. saprophyticus, the growth of S. carnosus, S. xylosus, and S. sciuri is substantially suppressed, so that detection of such strains as false-positive strains can be prevented. When the concentration of colistin sodium methanesulfonate is 4.1 mg/cm$^3$ (1.6 mg/ml in terms of mass concentration relative to the total volume of a sample to be added to the dried culture layer in the aspect of the microorganism culture substrate) or less, the growth of major S. aureus strains to be detected in the art is not inhibited, and such strains can be detected as a positive strains. When the concentration of colistin sodium methanesulfonate is 2.8 mg/cm$^3$ (1.1 mg/ml in terms of mass concentration relative to the total volume of a sample to be added to the dried culture layer in the aspect of the microorganism culture substrate) or less, in particular, the growth of approximately all the S. aureus strains to be detected in the art is not inhibited, and such strains can be detected as positive strains. With the use of the medium according to the present aspect containing colistin sodium methanesulfonate at high concentration as described above, accordingly, detection of the staphylococcal bacteria other than *S. aureus* as false-positive strains can be substantially prevented.

The medium according to the present aspect can contain one or more additional selection agents, according to need. Such one or more additional selection agents can be adequately selected from among compounds having antibacterial activity that are commonly used in the art as selection agents to be added to a medium used for detecting *S. aureus*. Examples of one or more additional selection agents include, but are not limited to, lithium chloride, lithium sulfate, sodium chloride, sodium azide, potassium tellurite, nalidixic acid, deferoxamine, aztreonam, and bacitracin. Such one or more additional selection agents are preferably a combination of lithium chloride, sodium azide, and nalidixic acid. A person skilled in the art can adequately determine the concentration of one or more additional selection agents within the range that is generally adopted in the art on the basis of, for example, conditions of the medium according to the present aspect and/or a sample containing the target microorganisms at the time of use, the volume thereof, and/or the culture condition. The concentration of lithium chloride is, for example, preferably 1 to 40 mg/cm$^3$. The concentration of sodium azide is, for example, preferably 20 to 200 μg/cm$^3$. The concentration of nalidixic acid is, for example, preferably 10 to 40 μg/cm$^3$. Such concentrations are defined as mass concentration relative to the total volume of the medium according to the present aspect. When an aspect of the present invention concerns a microorganism culture substrate used for detecting *S. aureus*, for example, such concentrations are defined as mass concentration relative to the total volume of the dried culture layer comprising the medium according to the present aspect. With the use of the medium according to the present aspect comprising one or more additional selection agents, detection of the staphylococcal bacteria other than *S. aureus* and other microorganisms as false-positive strains can be substantially prevented.

The concentration of a selection agent such as colistin sodium methanesulfonate contained in the medium according to the present aspect can be determined by, for example, purifying the selection agent contained in a certain volume of the medium with one or more separation means selected from among, for example, solvent extraction, distillation, recrystallization, and chromatography such as adsorption, partition and gel filtration, and quantitatively analyzing the selection agent with an analytic means, such as liquid chromatography/mass analysis (LC/MS).

The medium according to the present aspect contains a color developer that develops color in the presence of α-glucosidase that is known as an exoenzyme of *S. aureus*. Examples of color developers that develop color in the presence of α-glucosidase include, but are not limited to, 6-chloro-3-indoxyl-α-D-glucoside (pink), 6-bromo-3-indoxyl-α-D-glucoside (red), 5-bromo-4-chloro-3-indoxyl-α-D-glucoside (light blue), 5-bromo-4-chloro-3-indoxyl-N-methyl-α-D-glucoside (green), 5-bromo-6-chloro-3-indoxyl-α-D-glucoside (magenta), and 5-bromo-3-indoxyl-α-D-glucoside (blue). Such color developers are enzyme substrates that develop color in the presence of α-glucosidase. With reference to an embodiment in which the color developer is 6-chloro-3-indoxyl-α-D-glucoside, for example, when the target microorganism expresses α-glucosidase, 6-chloro-3-indoxyl-α-D-glucoside contained in the medium is hydrolyzed to glucose and an indole compound (6-chloro-3-indole) as the microorganism grows. The resulting indole compound is further dimerized, and the resultant turns pink. Other color developers are also hydrolyzed and dimerized, and the colors indicated in the parentheses are then developed.

The medium according to the present aspect contains a color developer that develops color in the presence of phosphatase that is known as an exoenzyme of *S. aureus*. Examples of color developers that develop color in the presence of phosphatase include, but are not limited to, 5-bromo-3-indoxyl phosphate (blue), 6-chloro-3-indoxyl phosphate (pink), 6-bromo-3-indoxyl phosphate (red), 5-bromo-4-chloro-3-indoxyl phosphate (light blue), and 5-bromo-6-chloro-3-indoxyl phosphate (magenta). Such color developers are enzyme substrates that develop color in the presence of phosphatase. With reference to an embodiment in which the color developer is 5-bromo-3-indoxyl phosphate, for example, when the target microorganism expresses phosphatase, 5-bromo-3-indoxyl phosphate contained in the medium is hydrolyzed to phosphoric acid and an indole compound (5-bromo-3-indole) as the microorganism grows. The resulting indole compound is further dimerized, and the resultant turns blue to dark blue. Other color developers are also hydrolyzed and dimerized, and the color indicated in the parentheses are then developed.

The medium according to the present aspect comprises a color developer that develops color in the presence of α-glucosidase and a color developer that develops color in the presence of phosphatase. The color developer that develops color in the presence of α-glucosidase is preferably 6-chloro-3-indoxyl-α-D-glucoside, and the color developer that develops color in the presence of phosphatase is preferably 5-bromo-3-indoxyl phosphate. Alternatively, the color developer that develops color in the presence of α-glucosidase is preferably 5-bromo-4-chloro-3-indoxyl-α-D-glucoside, and the color developer that develops color in the presence of phosphatase is preferably 5-bromo-6-chloro-3-indoxyl phosphate. *S. aureus* has the ability to produce α-glucosidase and the ability to produce phosphatase. When *S. aureus* is present in the medium according to the present aspect in which, for example, the color developer that develops color in the presence of α-glucosidase is 6-chloro-3-indoxyl-α-D-glucoside and the color developer that develops color in the presence of phosphatase is 5-bromo-3-indoxyl phosphate, accordingly, the colony formed by such strain was deduced to turn, for example, purple, which is a mixed color of pink developed by α-glucosidase activity and blue to dark blue developed by phosphatase activity. When *S. aureus* was present in the medium according to the present aspect containing the color developers in combination as described, surprisingly, it has been found that the strain grew and the resulting colony turned blue to dark blue. When *S. intermedius* having both the ability to produce α-glucosidase and the ability to produce phosphatase among staphylococcal bacteria other than *S. aureus* is present in the medium according to the present aspect containing the color developers in combination as described, in contrast, the strain grows and the resulting colony turns purple. When, among staphylococcal bacteria other than *S. aureus*, staphylococcal bacteria other than *S. intermedius*, such as *S. saprophyticus* subsp. *saprophyticus*, *S. carnosus*, *S. xylosus*, or *S. sciuri*, are present in the medium according to the present aspect containing the color developers in combination as described, the growth of the strain is inhibited by the highly concentrated colistin sodium methanesulfonate. Thus, the strain cannot exert the ability to produce α-glucosidase and/or the ability to produce phosphatase, and no color is developed. When *Bacillus* bacteria other than staphylococci are present in the medium according to the present aspect containing the color developers in combination as described, in addition, the growth of the strain is inhibited. Alternatively, the strain occasionally grows, and the resulting colony turns pink. When *S. aureus* is present in the medium according to the present aspect in which a color developer that develops color in the presence of α-glucosidase is 5-bromo-4-chloro-3-indoxyl-α-D-glucoside, and a color developer that develops color in the presence of phosphatase is 5-bromo-6-chloro-3-indoxyl phosphate, it has been found that the strain would grow and the resulting colony would turn magenta. When, among staphylococcal bacteria other than *S. aureus, S. intermedius* having both the ability to produce α-glucosidase and the ability to produce phosphatase is present in the medium according to the present aspect containing the color developers in combination described above, in contrast, the strain grows and the resulting colony turns gray. When, among staphylococcal bacteria other than *S. aureus*, staphylococcal bacteria other than *S. intermedius*, such as *S. saprophyticus* subsp. *saprophyticus, S. xylosus*, or *S. sciuri*, are present in the medium according to the present aspect containing the color developers in combination described above, the growth of the strain is inhibited by the highly concentrated colistin sodium methanesulfonate. Thus, the strain cannot exert the ability to produce α-glucosidase and/or the ability to produce phosphatase, and no color is developed. When *Bacillus* bacteria other than staphylococci are present in the medium according to the present aspect containing the color developers in combination described above, the growth of the strain is inhibited, or the strain occasionally grows and the resulting colony turns gray or blue. With the use of the medium according to the present aspect containing colistin sodium methanesulfonate at high concentration in addition to the two types of color developers, accordingly, *S. aureus* can be selectively detected with high accuracy without detecting staphylococcal bacteria other than *S. aureus* and other microorganisms as false-positive strains.

The medium according to the present aspect can contain at least one solvent, according to need. Examples of at least one solvent include, but are not limited to, water, a lower alcohol (e.g., an alcohol having 1 to 6 carbon atoms such as methanol, ethanol, or 2-propanol (isopropyl alcohol)), a higher alcohol (e.g., an alcohol having 7 or more carbon atoms such as 1-heptanol or 1-octanol), and dimethyl sulfoxide (DMSO). At least one solvent is preferably water. With the use of the solvent, which is preferably water, the medium according to the present aspect containing the solvent enables detection of the target of detection (i.e., *S. aureus*) with high accuracy while refraining from inhibiting the growth thereof.

The medium according to the present aspect can be used in the form of either a solid medium or liquid medium. When the medium according to the present aspect is a liquid medium, it can be used for liquid culture while it is accommodated in a culture vessel that is generally used in the art, such as a flask, petri dish, tube, or multi-well plate.

When the medium according to the present aspect is a solid medium, it can be used in any form. In this embodiment, for example, the medium according to the present aspect can be used in the form of a plane solid medium accommodated in a culture vessel that is generally used in the art, such as a petri dish or multi-well plate, or in the form of a culture substrate in which the medium is provided on an upper surface of the substrate in a desired form. In the embodiment of a solid medium, in general, the medium according to the present aspect contains one or more gelling agents. One or more gelling agents can be adequately selected from among compounds that are generally used in the art as gelling agents that solidify a medium used for detecting *S. aureus*. Examples of one or more gelling agents include, but are not limited to, carragheenan, xanthan gum, Locust bean gum, psyllium seed gum, guar gum, hydroxyethyl cellulose, carboxymethyl cellulose, alginic acid, alginate, agar, and gelatin. One or more gelling agents are preferably a combination of psyllium seed gum and guar gum. A person skilled in the art can adequately determine the concentration of one or more gelling agents within the range that is generally adopted in the art on the basis of, for example, conditions of the medium according to the present aspect and/or a sample containing the target microorganisms at the time of use, volumes thereof, and/or culture conditions.

The medium according to the present aspect with the features described above enables selective detection of *S. aureus* with high accuracy without detecting coexisting staphylococci and other microorganisms as false-positive strains.

<2: Microorganism Culture Substrate Used for Detecting *Staphylococcus aureus*>

The medium according to an aspect of the present invention can be used as a solid medium of any configuration. Accordingly, another aspect of the present invention relates to a microorganism culture substrate used for detecting *S. aureus*, which comprises a substrate and a culture layer provided on an upper surface of the substrate comprising the medium according to the present invention.

According to the present aspect, the configuration of the substrate can be adequately selected from among various configurations that are generally employed in the art, such as a sheet, film, plate, or vessel (e.g., a circular or square petri dish).

According to the present aspect, the configuration of the culture layer is not particularly limited, and it can be adequately selected in accordance with, for example, the configuration of the substrate. According to the present aspect, the culture layer comprises the medium according to an aspect of the present invention. The medium according to an aspect of the present invention contained in the culture layer of the microorganism culture substrate according to the present aspect has the features described above. Accordingly, the microorganism culture substrate according to the present aspect enables selective detection of *S. aureus* with high accuracy without detecting coexisting staphylococci and other microorganisms as false-positive strains.

The microorganism culture substrate according to the present aspect preferably has a sheet-formed substrate (hereafter, it is also referred to as a "substrate sheet"). The microorganism culture substrate according to the present aspect having a substrate sheet (hereafter, it is also referred to as a "microorganism culture sheet used for detecting *S. aureus*" or simply as a "microorganism culture sheet") can comprise a substrate sheet, a culture layer provided on an upper surface of the substrate sheet, and a cover sheet covering the culture layer. In such a case, the culture layer comprises, for example, the medium according to an aspect of the present invention, one or more fixing agents, and one or more gelling agents.

A microorganism culture sheet having a substrate sheet and a culture layer containing a solid medium provided on an upper surface of the substrate sheet is known in the art. Such microorganism culture sheet is disclosed in, for example, International Publication WO 2011/007802 and JP 2014-90701 A. Any configuration of a microorganism culture sheet disclosed in the above literature and known in the art can be adopted for the microorganism culture substrate used for detecting *S. aureus* according to the present aspect.

FIG. 1 shows an embodiment of a microorganism culture substrate used for detecting *S. aureus* according to the present aspect. In FIG. 1, (a) shows a top view of the microorganism culture substrate according to the present aspect; (b) shows a schematic side cross sectional view taken along I-I' in (a); and (c) shows a schematic side cross sectional view showing a culture layer covered with a folded cover sheet. The microorganism culture sheet having a sheet-formed substrate, which is an embodiment of the microorganism culture substrate according to the present aspect, comprises: a substrate sheet 10; a culture layer 30 provided on an upper surface of the substrate sheet 10; and a cover sheet 40 covering the culture layer 30, as shown in, for example, FIG. 1. The substrate sheet 10 may be a single-layered sheet or a multi-layered sheet composed of a laminate of a plurality of sheets made of the same or different materials. Also, the cover sheet 40 may be a single-layered sheet or a multi-layered sheet composed of a laminate of a plurality of sheets made of the same or different materials. Further, the culture layer 30 may be of a single-layered structure or a multi-layered structure composed of a laminate of a plurality of layers having the same or different compositions. When the culture layer 30 is of a multi-layered structure, it is sufficient if at least one layer contains the medium according to the present aspect.

The configuration of the substrate sheet and that of the cover sheet of the microorganism culture sheet according to the present embodiment are not particularly limited. For example, the configuration of the substrate sheet 10 and that of the cover sheet 40 may be a square, another polygon such as a triangle, a circle such as a true or oval circle, or irregular. The configuration of the substrate sheet 10 may be the same with or different from that of the cover sheet 40. The size of the substrate sheet 10 may be the same with or different from that of the cover sheet 40. The configuration and the size of the substrate sheet 10 are preferably the same with those of the cover sheet 40. In such a case, the cover sheet 40 covers the entire upper surface of the substrate sheet 10 on which the culture layer 30 is provided, so that the culture layer 30 can be protected.

The configuration of the culture layer of the microorganism culture sheet according to the present embodiment is not particularly limited. For example, the configuration of the culture layer 30 may be a circle such as a true or oval circle, a polygon, such as a square (i.e., a true or oblong square) or triangle, or irregular, as shown in FIG. 1. The size of the culture layer 30 can be adequately determined, as long as it can be provided on an upper surface of the substrate sheet 10. The culture layer 30 is preferably a circle. In such a case, the sample may be added to an area in the vicinity of the center of the culture layer 30, so that the sample can be uniformly dispersed throughout the culture layer 30.

Figure 2:
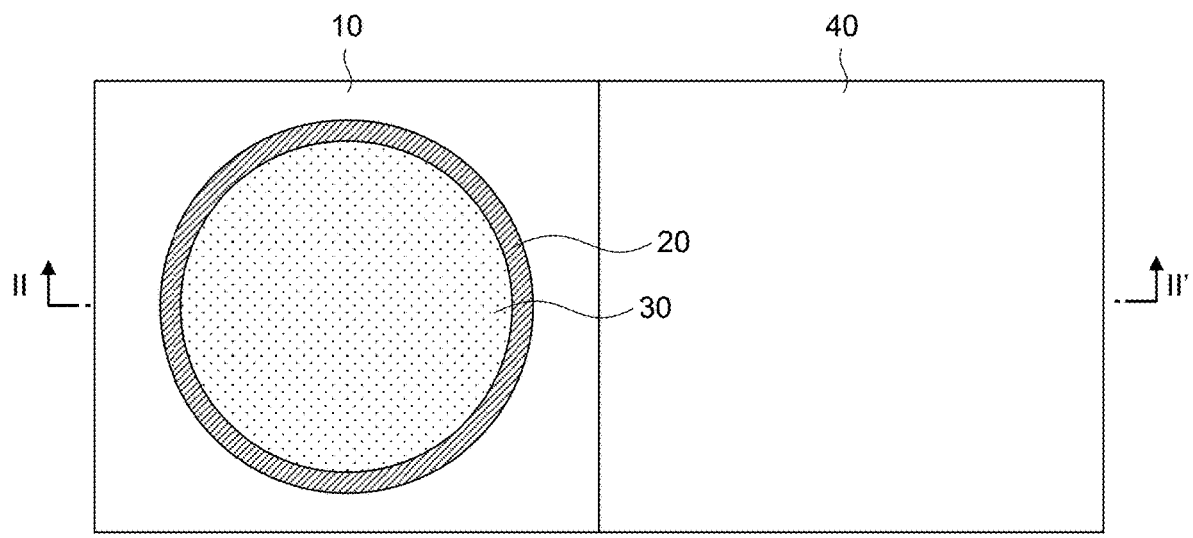
FIG. 2 shows another embodiment of the microorganism culture substrate used for detecting *S. aureus* according to an aspect of the present invention; (a): a top view of the microorganism culture substrate according to an aspect of the present invention; (b): a schematic side cross sectional view taken along II-II' in (a); and (c): a schematic side cross sectional view showing a culture layer covered with a folded cover sheet.
Figure 2:
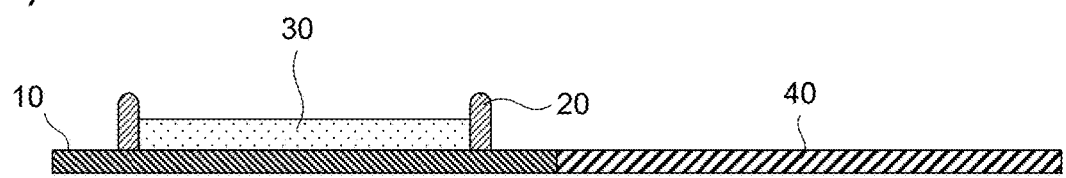
Figure 2:
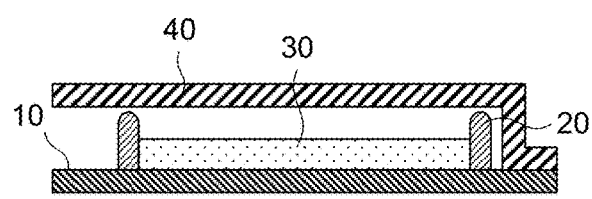
Figure 3:
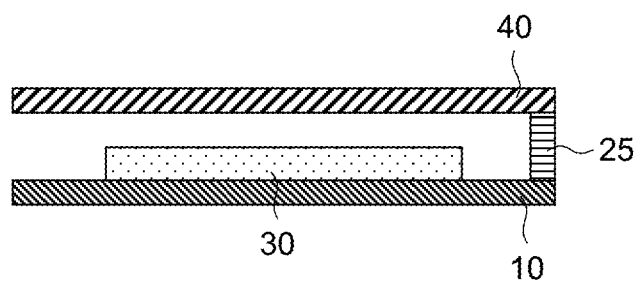
FIG. 3 is a schematic side cross sectional view showing another embodiment of the microorganism culture substrate used for detection of *S. aureus* according to an aspect of the present invention.
Figure 4:
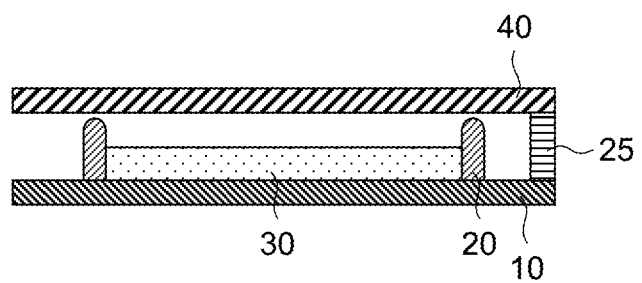
FIG. 4 is a schematic side cross sectional view showing another embodiment of the microorganism culture substrate used for detecting *S. aureus* according to an aspect of the present invention.

In the microorganism culture sheet according to the present embodiment, the cover sheet is preferably fixed to the substrate sheet. A means for fixing the cover sheet is not particularly limited. For example, the cover sheet 40 can be directly fixed onto the substrate sheet 10 by any means such as pressure bonding, as shown in FIGS. 1 and 2. Alternatively, the cover sheet 40 can be fixed to the substrate sheet 10 with the aid of a fixing member 25, such as a double-sided tape or adhesive, as shown in FIGS. 3 and 4.

The microorganism culture substrate used for detecting *S. aureus* according to the present aspect can have a frame layer provided to surround the outer periphery of the culture layer, according to need. FIG. 2 shows another embodiment of the microorganism culture substrate used for detecting *S. aureus* according to the present aspect. In FIG. 2, (a) shows a top view of the microorganism culture substrate according to the present aspect; (b) shows a schematic side cross sectional view taken along II-II' in (a); and (c) shows a schematic side cross sectional view showing a culture layer covered with a folded cover sheet. The microorganism culture sheet having a sheet-formed substrate, which is an embodiment of the microorganism culture substrate according to the present aspect, comprises: a substrate sheet 10; a culture layer 30 provided on an upper surface of the substrate sheet 10; a frame layer 20 provided to surround the culture layer 30; and a cover sheet 40 covering the culture layer 30, as shown in, for example, FIG. 2. When the microorganism culture sheet has the frame layer 20, the area in which a sample is allowed to spread can be limited to the area within the culture layer 30 at the time of the addition of the sample to the culture layer 30. The frame layer 20 may be provided to be in close contact with or distant from the outer periphery of the culture layer 30. The frame layer 20 is preferably provided to be in close contact with the outer periphery of the culture layer 30. Thus, the area in which a sample is allowed to spread can be definitely limited to the area within the culture layer 30 at the time of the addition of the sample to the culture layer 30. The configuration of the frame layer 20 is not particularly limited, and a person skilled in the art can select an adequate configuration in accordance with the configuration of the culture layer 30. For example, the configuration of the frame layer 20 may be a circle such as a true or oval circle, a polygon, such as a square (i.e., a true or oblong square) or triangle, or irregular, as shown in FIG. 2. The frame layer 20 is preferably a circle, and it is more preferably a circle and provided to be in close contact with the outer periphery of the culture layer 30. With the addition of a sample in an area in the vicinity of the center of the culture layer 30, the sample is allowed to uniformly spread over the entire area of the culture layer 30, and the area in which the sample is allowed to spread can be definitely limited to the area within the culture layer 30.

When the microorganism culture substrate used for detecting *S. aureus* according to the present aspect comprises the culture layer and the frame layer (in a case where it is present), at least one culture layer and at least one frame layer may be provided on an upper surface of the substrate. Specifically, a plurality of culture layers and frame layers (in a case where they are present) may be provided on an upper surface of the substrate. In such embodiment, a plurality of culture layers and frame layers (in a case where they are present) can be provided at any positions on an upper surface of the substrate.

A person skilled in the art can adequately determine the size of the microorganism culture substrate used for detecting *S. aureus* according to the present aspect in accordance with, for example, the volume of the target microorganism-containing sample. In the embodiment of a microorganism culture sheet having a sheet-formed substrate in which the configuration of the substrate sheet 10 is square, for example, a length of a side of the substrate sheet 10 is generally 50 to 100 mm, and typically 70 to 90 mm. A thickness thereof is generally 25 to 1500 μm, and typically 50 to 500 μm. The configuration and the size of the cover sheet 40 are preferably the same with those of the substrate sheet 10. A thickness of the cover sheet 40 is preferably 10 to 200 μm, and more preferably 20 to 70 μm. When the configuration of the culture layer 30 is circular, a diameter of the culture layer 30 is preferably 20 to 80 mm, and more preferably 30 to 70 mm. When the configuration of the culture layer 30 is not circular, a diameter of the maximal circle inscribed in the figure defined by the outer periphery of the culture layer 30 is preferably within the range described above. A thickness of the culture layer 30 is preferably 150 to 250 μm, and more preferably 190 to 210 μm. A thickness of the culture layer 30 is defined as an average distance from the lower surface of the dried culture layer 30 (i.e., the surface that is in contact with the substrate sheet 10) to the upper surface of the culture layer 30 of the microorganism culture sheet according to the present embodiment. A thickness of the culture layer 30 can be determined by measuring, for example, the distance between the lower surface and the upper surface of the substrate sheet 10 and the distance between the lower surface of the substrate sheet 10 and the upper surface of the dried culture layer 30 at several positions and calculating the average of differences in both distances. When the size of the culture layer 30 is within the range described above, a given amount of a sample can be absorbed and retained with certainty.

When the microorganism culture substrate used for detecting S. aureus according to the present aspect comprises a frame layer, a person skilled in the art can adequately determine the size of the frame layer in accordance with the size of the culture layer. In the embodiment of a microorganism culture sheet having a sheet-formed substrate, for example, a height of the frame layer 20 is preferably higher than the height of the culture layer 30 by 100 to 1200 μm, more preferably by 200 to 1000 μm, and further preferably by 300 to 800 μm. A width of the frame layer 20 is preferably 0.5 to 5.0 mm, and more preferably 1.0 to 3.0 mm. A height of the frame layer 20 is defined as an average distance from the lower surface of the frame layer 20 (i.e., the surface that is in contact with the substrate sheet 10) to the upper surface of the frame layer 20 of the microorganism culture sheet according to the present embodiment. A height of the frame layer 20 can be determined by measuring, for example, the distance between the lower surface and the upper surface of the substrate sheet 10 and the distance between the lower surface of the substrate sheet 10 and the upper surface of the frame layer 20 at several positions and calculating the average of differences in both distances. A width of the frame layer 20 is defined as an average distance between the side surfaces of the frame layer 20. When the size of the frame layer 20 is within the range described above, effusion of a sample occurring when the sample is added to the culture layer 30 can be prevented. When the culture layer 30 is covered with the cover sheet 40, generation of gaps between the cover sheet 40 and the culture layer 30 can be substantially prevented. Thus, a sample is allowed to spread in the culture layer 30 with certainty.

A substrate of the microorganism culture substrate according to the present aspect preferably comprises, as a main component, at least one plastic material selected from the group consisting of polyester, polyethylene, polypropylene, polystyrene, polycarbonate, and polyvinyl chloride. The substrate comprising the plastic material as a main component is water resistant and solvent resistant. Thus, a culture layer comprising water and/or a solvent can be provided on the upper surface of the substrate. Further, the substrate comprising the plastic material as a main component is heat resistant and it has printability. Thus, a culture layer can be provided on the upper surface of the substrate by means of, for example, printing, coating, or spraying. Furthermore, the substrate comprising the plastic material as a main component has excellent transparency. Thus, a microbial colony grown in the culture layer can be observed through the light penetrating the substrate. Alternatively, the substrate may be colored with the addition of a coloring agent or foaming agent to the plastic material or via other means and used in the colored state. With the use of the colored substrate, the color of the colony grown in the culture layer can be evaluated more apparently.

According to an embodiment of a microorganism culture sheet having a sheet-formed substrate in which a substrate sheet has a multi-layered structure, such substrate sheet may be a laminate of the sheets identical to each other mainly composed of the plastic material described above or a laminate of sheets different from each other. Alternatively, a substrate sheet of a multi-layered structure may be a laminate of sheets composed mainly of paper and/or synthetic resin and sheets composed mainly of the plastic material described above different from or identical to each other. Examples of substrate sheets of a multi-layered structure composed mainly of paper and synthetic resin include YUPO® (Yupo Corporation) and CRISPR® (Toyobo Co., Ltd.).

Figure 5:
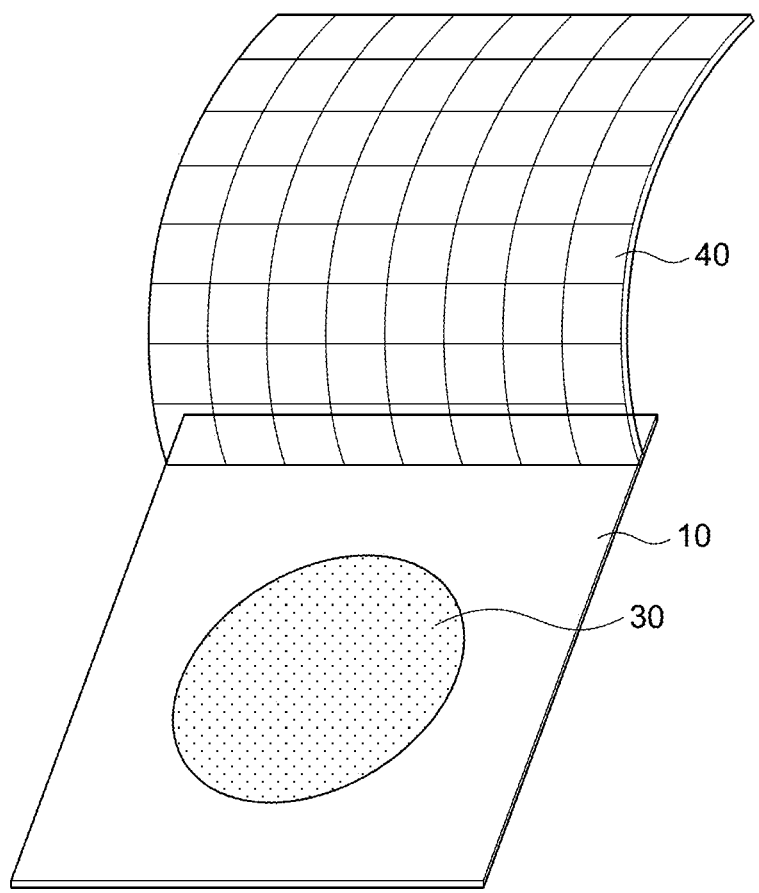
FIG. 5 is an external perspective view showing an embodiment of the microorganism culture substrate used for detecting *S. aureus* according to an aspect of the present invention.
Figure 6:
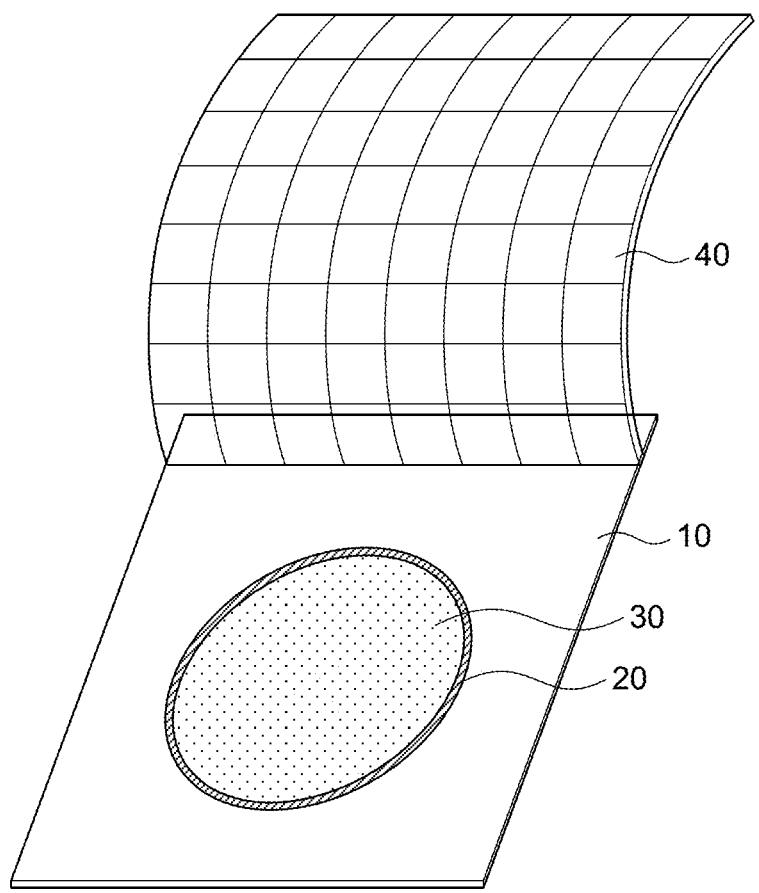
FIG. 6 is an external perspective view showing another embodiment of the microorganism culture substrate used for detecting *S. aureus* according to an aspect of the present invention.

In the microorganism culture sheet according to the embodiment of the present invention, a cover sheet is employed for the purpose of prevention of contamination of the culture layer and/or prevention of moisture evaporation from the culture layer. The cover sheet preferably comprises, as a main component, at least one plastic material selected from the group consisting of polyester, polyethylene, polypropylene, polystyrene, polycarbonate, and polyvinyl chloride. The cover sheet composed mainly of the plastic material has excellent transparency. Thus, a microbial colony grown in the culture layer can be observed through the light penetrating the cover sheet. The cover sheet 40 may have a squared pattern of a given size as an indicator of observation as shown in, for example, FIGS. 5 and 6. According to the present embodiment, a squared pattern can be formed by printing the pattern on the cover sheet surface using an ink that is insoluble in water and does not substantially influence the microbial growth.

The culture layer of the microorganism culture substrate according to the present aspect can comprise one or more fixing agents. In the present invention, the term "fixing agent" refers to a compound that modifies the viscosity of the medium contained in the culture layer and brings the culture layer into close contact with the surface of the substrate sheet. According to an embodiment of a microorganism culture sheet comprising a sheet-formed substrate, one or more fixing agents are preferably polyvinylpyrrolidone. With the use of polyvinylpyrrolidone as one or more fixing agents, the medium components contained in the culture layer can be uniformly dispersed. By increasing the viscosity of the medium according to an aspect of the present invention, also, a culture layer of the size of interest can be provided at a position of interest on the upper surface of the substrate sheet when producing the microorganism culture sheet according to the present embodiment. In addition, polyvinylpyrrolidone is highly adhesive to the substrate sheet composed mainly of the plastic material. Thus, the culture layer can be adhered to the surface of the substrate sheet without the use of an adhesive agent or the like. The concentration of polyvinylpyrrolidone used as one or more fixing agents is preferably 15 to 20%. Such concentration is defined as the final concentration (mass percentage) relative to the total mass of the dried culture layer in the microorganism culture sheet according to the present embodiment. By incorporating polyvinylpyrrolidone as one or more fixing agents, a culture layer with desired properties can be prepared.

The culture layer of the microorganism culture substrate according to the present aspect can comprise one or more gelling agents. As one or more gelling agents, gelling agents exemplified above as components of the medium according to an aspect of the present invention can be used. According to an embodiment of the microorganism culture sheet having a sheet-formed substrate, one or more gelling agents are preferably a combination of psyllium seed gum and guar gum. The concentration of one or more gelling agents is preferably 50 to 60%. Such concentration is defined as the final concentration (mass percentage) relative to the total mass of the dried culture layer in the microorganism culture sheet according to the present embodiment. By incorporating one or more gelling agents, a culture layer with desired properties can be prepared.

The culture layer of the microorganism culture substrate according to the present aspect comprises one or more plasticizers, according to need. Examples of one or more plasticizers include glycerin, a glycerin derivative-based plasticizer, and polyethylene glycol. According to an embodiment of a microorganism culture sheet having a sheet-formed substrate, one or more plasticizers are preferably glycerin. The concentration of one or more plasticizers is preferably 5 to 10%. Such concentration is defined as the final concentration (mass percentage) relative to the total mass of the dried culture layer in the microorganism culture sheet according to the present embodiment. By incorporating one or more plasticizers, plasticity, flexibility, elasticity, and other properties of the culture layer can be improved.

The microorganism culture sheet having a sheet-formed substrate according to the present aspect can be produced on the basis of any method for producing a microorganism culture sheet known in the art, which is disclosed in, for example, WO 2011/007802 or JP 2014-90701 A. The microorganism culture sheet according to the present embodiment can be produced by, for example, a method comprising a step of preparing a substrate sheet, a step of pattern forming a culture layer on an upper surface of the substrate sheet, and a step of fixing the substrate sheet and the cover sheet. When the microorganism culture sheet according to the present embodiment has a frame layer, it is preferable that the method of production described above further comprise a step of forming a frame layer on an upper surface of the substrate sheet.

In the method for producing the microorganism culture sheet according to the present embodiment, a step of pattern forming a culture layer on an upper surface of the substrate sheet further comprises: a step of preparing a medium liquid comprising the components of the culture layer suspended in one or more solvents; a step of applying the medium liquid to an upper surface of the substrate sheet; and a step of drying the applied medium liquid to form a culture layer with a given configuration. When preparing the medium liquid, one or more solvents used for viscosity modification or other purposes can be adequately selected from among the solvents exemplified above as components of the medium according to an aspect of the present invention. As one or more solvents used for medium liquid preparation, a lower alcohol is preferable, methanol, ethanol, or 2-propanol (isopropyl alcohol) is more preferable, and methanol is further preferable. In general, the medium liquid contains all the components contained in the culture layer in the step of preparation; however, it is not necessary for the medium liquid to contain some components contained in the culture layer in the step of preparation. In such a case, during the step of applying the medium liquid to the upper surface of the substrate sheet or at any time after the step, the remaining components may be added to the applied medium liquid or the formed culture layer.

The step of applying a medium liquid to an upper surface of the substrate sheet can be performed by means of, for example, printing, coating, or spraying. In the subsequent step of drying the applied medium liquid, a solvent contained in the medium liquid may be removed by evaporation to form a culture layer of a given configuration. Polyvinylpyrrolidone contained in the culture layer is highly adhesive to the substrate sheet composed mainly of the plastic material described above. By performing the step of applying a medium liquid to an upper surface of the substrate sheet and the subsequent step of drying the applied medium liquid, accordingly, the culture layer can be adhered to the surface of the substrate sheet without the use of an adhesive agent or the like.

The method for producing the microorganism culture sheet according to the present embodiment may further comprise a step of sterilizing the obtained microorganism culture sheet. Examples of means for sterilizing the microorganism culture sheet include sterilization via application of radioactive rays such as gamma rays and chemical sterilization with the use of ethylene oxide gas.

By performing the method comprising the steps described above, the microorganism culture sheet having a sheet-formed substrate can be produced.

<3: Method for Detecting *Staphylococcus aureus*>

The medium and the microorganism culture substrate according to an aspect of the present invention can be used for selectively detecting *S. aureus* with high accuracy from a sample containing many microorganisms including staphylococcal bacteria other than *S. aureus*. Accordingly, another aspect of the present invention relates to a method for detecting *S. aureus* with the use of the medium and the microorganism culture substrate according to an aspect of the present invention. The method for detecting *S. aureus* according to the present aspect comprises a step of sample addition, a step of colony formation, and a step of strain identification.

[3-1: Step of Sample Addition]

This step comprises adding a microorganism-containing sample to the medium and the culture layer of the microorganism culture substrate according to an aspect of the present invention.

A sample used in this step generally contains *S. aureus*, and the sample occasionally contains *S. aureus* and further microorganisms other than *S. aureus*. As described above, the medium and the microorganism culture substrate according to an aspect of the present invention enable selective detection of *S. aureus* with high accuracy from a sample containing further microorganisms such as staphylococcal bacteria other than *S. aureus*. Accordingly, the further microorganisms contained in the sample are not particularly limited. Examples of the further microorganisms contained in the sample include, but are not limited to, bacteria of non-staphylococcal bacteria, such as *Escherichia coli*, *Enterococcus*, and *Bacillus* bacteria, in addition to staphylococcal bacteria other than *S. aureus*. By the method according to the present aspect, *S. aureus* can be selectively detected with high accuracy from samples containing many microorganisms exemplified above.

A microorganism-containing sample can be prepared from any target, such as a product (e.g., a food, beverage, medical, or animal feed product), equipment, apparatus, and place in which *S. aureus* may be present.

In this step, a microorganism-containing sample is generally used in the form of liquid. In such a case, a solvent of the sample is generally sterile water. A solvent can contain an inorganic salt, buffer, medium, and other components, according to need.

In this step, a person skilled in the art can adequately determine the volume of a sample to be added to the medium and the culture layer of the microorganism culture substrate according to an aspect of the present invention in accordance with, for example, the size of the medium and the culture layer of the microorganism culture substrate according to an aspect of the present invention. In the embodiment of the microorganism culture substrate according to an aspect of the present invention having the sheet-formed substrate as shown in FIG. 1; i.e., the microorganism culture sheet, for example, about 1 ml of a sample is preferably added. With the addition of a sample in the volume described above, the added sample can be absorbed and retained by the culture layer with certainty.

When the microorganism culture substrate according to an aspect of the present invention, for example, the microorganism culture sheet, is used in this step, the culture layer of the microorganism culture substrate preferably comprises colistin sodium methanesulfonate at 0.2 mg/ml or more relative to the total volume of the microorganism-containing sample. In such a case, the concentration of colistin sodium methanesulfonate contained in the culture layer of the microorganism culture substrate is preferably 0.2 to 1.6 mg/ml, more preferably 0.2 to 1.1 mg/ml, further preferably 0.9 to 1.1 mg/ml, and particularly preferably about 1 mg/ml. With the use of the microorganism culture substrate containing colistin sodium methanesulfonate at the high concentration as described above, detection of the staphylococcal bacteria other than $S.$ $aureus$ as false-positive strains can be substantially prevented.

In the method according to the present aspect, $S.$ $aureus$ is identified on the basis of the color of the colony formed in the medium and the culture layer of the microorganism culture substrate according to an aspect of the present invention. When the cell density of the microorganisms contained in the sample is high, accordingly, it may be difficult to separate and identify the resulting colonies as a plurality of single colonies. It is thus preferable to dilute the microorganism-containing sample with a solvent in advance to adjust the cell density to an adequate level. A person skilled in the art can adequately determine the cell density of the microorganisms contained in a sample in accordance with the volume of the sample added and the size of the medium used and the culture layer of the microorganism culture substrate according to an aspect of the present invention. In the embodiment of the microorganism culture substrate according to an aspect of the present invention having a sheet-formed substrate as shown in FIG. 1; i.e., the microorganism culture sheet, for example, the cell density of the microorganisms contained in a sample is preferably 1 to 500 cfu/ml. When the cell density of the microorganisms contained in a sample is within the range described above, all the microorganisms contained in the sample can be separated and identified as a single colony in the culture layer with the addition of about 1 ml of the sample to the culture layer.

[3-2: Step of Colony Formation]

This step comprises incubating the medium or microorganism culture substrate supplemented with a sample to form microbial colonies.

A person skilled in the art can adequately determine conditions for incubation of the medium or microorganism culture substrate supplemented with a sample in accordance with the conditions for culture of microorganisms such as $S.$ $aureus$ generally employed in the art.

[3-3: Step of Strain Identification]

This step comprises identifying $S.$ $aureus$ on the basis of the color of the formed microbial colony.

When $S.$ $aureus$ is present in the medium or the culture layer of the microorganism culture substrate according to an aspect of the present invention in which, for example, a color developer that develops color in the presence of α-glucosidase is 6-chloro-3-indoxyl-α-D-glucoside and a color developer that develops color in the presence of phosphatase is 5-bromo-3-indoxyl phosphate, as described above, the colony formed by such strain turns blue to dark blue. When, among staphylococcal bacteria other than $S.$ $aureus$, $S.$ $intermedius$ having both the ability to produce α-glucosidase and the ability to produce phosphatase is present in the medium or the culture layer of the microorganism culture substrate according to an aspect of the present invention that contains the color developers in combination described above, in contrast, the colony formed by such strain turns purple. When staphylococcal bacteria other than $S.$ $intermedius$, such as $S.$ $saprophyticus$ subsp. $saprophyticus$, $S.$ $carnosus$, $S.$ $xylosus$, or $S.$ $sciuri$ among staphylococcal bacteria other than $S.$ $aureus$, are present in the medium or the culture layer of the microorganism culture substrate according to an aspect of the present invention that contains the color developers in combination described above, for example, the growth of the strain is inhibited by the highly concentrated colistin sodium methanesulfonate, the strain cannot exert the ability to produce α-glucosidase and/or the ability to produce phosphatase, and the color is not developed. When bacteria of $Bacillus$ other than $staphylococcus$ are present in the medium or the culture layer of the microorganism culture substrate according to an aspect of the present invention that contains the color developers in combination described above, in addition, the growth of the strain is inhibited. Alternatively, the strain may grow and the resulting colony may turn pink. When $S.$ $aureus$ is present in the medium or the culture layer of the microorganism culture substrate according to an aspect of the present invention in which a color developer that develops color in the presence of α-glucosidase is 5-bromo-4-chloro-3-indoxyl-α-D-glucoside and a color developer that develops color in the presence of phosphatase is 5-bromo-6-chloro-3-indoxyl phosphate, further, the colony formed by such strain turns magenta. When $S.$ $intermedius$ having both the ability to produce α-glucosidase and the ability to produce phosphatase among staphylococcal bacteria other than $S.$ $aureus$ is present in the medium or the culture layer of the microorganism culture substrate according to the present aspect that contains the color developers in combination described above, in contrast, the strain grows, and the resulting colony turns gray. When, among staphylococcal bacteria other than $S.$ $aureus$, staphylococcal bacteria other than $S.$ $intermedius$, such as $S.$ $saprophyticus$ subsp. $saprophyticus$, $S.$ $xylosus$, or $S.$ $sciuri$, is present in the medium or the culture layer of the microorganism culture substrate, the growth of the strain is inhibited by colistin sodium methanesulfonate at high concentration. Thus, the ability to produce α-glucosidase and/or the ability to produce phosphatase are not expressed, and the color is not developed. When bacteria of $Bacillus$ other than staphylococci are present in the medium or the culture layer of the microorganism culture substrate according to the present aspect that contains the color developers in combination described above, the growth of the strain is inhibited, or the strain grows and the resulting colony turns gray or blue. Therefore, *S. aureus* could be identified with high accuracy on the basis of the color of the formed microbial colony.

As described above, the medium and the microorganism culture substrate according to an aspect of the present invention enable selective detection of *S. aureus* without detecting staphylococcal bacteria other than *S. aureus* as false-positive strains. With the use of the medium and the microorganism culture substrate according to an aspect of the present invention, accordingly, *S. aureus* in various targets can be selected rapidly with high accuracy.

EXAMPLES

The present invention is described in greater detail with reference to the following examples. However, the technical scope of the present invention is not limited to these examples.

<I: Production of Microorganism Culture Sheet>

As a substrate sheet 10, a synthetic paper composed mainly of synthetic resin was prepared (YUPO®, Yupo Corporation). The configuration of the substrate sheet 10 was oblong. The thickness of the substrate sheet 10 was 270 μm, the length of a longer side of the substrate sheet 10 was 90 mm, and the length of a shorter side of the substrate sheet 10 was 72 mm.

A circular frame layer 20 made of ethylene-vinyl acetate-based hot-melt resin was provided on an upper surface of the substrate sheet 10. The width of the frame layer 20 (the gap between the outer periphery and the inner periphery of the frame layer 20) was 1 mm, the inner diameter of the frame layer 20 (a diameter of a circle defined by the inner periphery) was 50 mm, and the height of the frame layer 20 was 750 μm.

A medium liquid for forming a culture layer 30 was applied in a region surrounded by the frame layer 20 on an upper surface of the substrate sheet 10. The medium liquid comprises solid components, including nutrient components, a color developer, a selection agent, a fixing agent, a gelling agent and a plasticizer, and a solvent for viscosity modification (methanol). As nutrient components, tryptone, soytone, yeast extract, sodium pyruvate, D(−)-mannitol, potassium phosphate, and glycine were used. Solid components included in the medium liquid are shown in Table 1.

The medium liquid applied to the substrate sheet 10 was dried to remove methanol via evaporation, and the culture layer 30 was formed on an upper surface of the substrate sheet 10. A thickness of the culture layer 30 was 200 μm. The thickness of the culture layer 30 was determined by measuring the distance between the lower surface and the upper surface of the substrate sheet 10 and the distance between the lower surface of the substrate sheet 10 and the upper surface of the dried culture layer 30 at 5 positions and calculating the average of differences in both distances.

On the upper surface of the substrate sheet 10, a double-sided tape with a length of 6 mm and a width of 72 mm was applied as a fixing member 25 along a shorter side of the substrate sheet 10. Subsequently, a cover film 40 having a substrate layer, a printed layer, and a water repellent layer was prepared. The substrate layer was formed of transparent oriented polypropylene with a thickness of 40 μm. On the printed layer, lines defining squares with intervals of 10 mm were provided. The water repellent layer was formed of resin mainly composed of polyamide. The length of a longer side of the cover film 40 was 95 mm, and the length of a shorter side thereof was 72 mm. Subsequently, a region in the vicinity of a shorter side of the cover film 40 was bonded to the substrate sheet 10 via the fixing member 25. Thus, the microorganism culture sheet was produced.

<II: Detection of Microorganism>

Experiment 1: Test for Detecting Microorganisms Using a Medium Containing a Color Developer that Develops Color in the Presence of α-Glucosidase A given type of microbial strains to be tested were inoculated into a liquid medium (SCD broth medium), and culture was conducted at 35° C. for 24 hours to prepare a test microbial suspension. This test microbial suspension was diluted with phosphate buffered physiological saline to adjust the cell density to about 1 to 500 cfu/ml. The resulting test microbial sample (1 ml) was inoculated into the culture layer of the microorganism culture sheet prepared with the use of the medium liquid containing the components shown in Table 1 using a micropipette. The microorganism culture sheet into which the sample had been inoculated was allowed to stand in an incubator and culture was then conducted at 35° C. for 24 or 48 hours. After the completion of culture, the microorganism culture sheet was removed from the incubator. The color of the colony formed in the culture layer of the microorganism culture sheet and the color intensity were visually inspected. Each test microbial strain was subjected to the experiment described above. The names of the microbial strains to be tested used for the experiment and the conditions and the color of the colonies formed by the strains are shown in Table 2.

TABLE 1

| Components | Experiment 1 | Experiment 2 | Experiment 3 |
|---|---|---|---|
| Nutrient component | 56 | 56 | 56 |
| Lithium chloride | 16.8 | 16.8 | 16.8 |
| Sodium azide | 0.05 | 0.05 | 0.05 |
| Nalidixic acid | 0.019 | 0.019 | 0.019 |
| 6-Chloro-3-indoxyl-α-D-glucoside | 0.83 | — | 0.83 |
| 5-Bromo-3-indoxyl phosphate | — | 0.83 | 0.83 |
| Polyvinylpyrrolidone | 59 | 59 | 59 |
| Psyllium seed gum | 72 | 72 | 72 |
| Guar gum | 107 | 107 | 107 |
| Glycerin | 23.5 | 23.5 | 23.5 |

TABLE 2

| Strain | Culture for 24 hours | | Culture for 48 hours | |
|---|---|---|---|---|
| | Colony formation | Color | Colony formation | Color |
| *Staphylococcus aureus* ATCC25923 | Occurred | Pink | Occurred | Pink |
| *Staphylococcus aureus* NBRC100910 | Occurred | Pink | Occurred | Pink |
| *Staphylococcus aureus* NBRC12732 | Occurred | Pink | Occurred | Pink |
| *Staphylococcus intermedius* ATCC29663 | Occurred | Pink | Occurred | Pink |
| *Staphylococcus hyicus* ATCC11249 | Occurred | No color | Occurred | Pink |
| *Staphylococcus epidermidis* NBRC12993 | Occurred | No color | Occurred | Pink |
| *Staphylococcus saprophyticus* subsp. *saprophyticus* NBRC102446 | Occurred | Pink | Occurred | Pink |
| *Staphylococcus xylosus* NBRC109770 | Occurred | No color | Occurred | Pink |
| *Staphylococcus sciuri* ATCC29062 | Occurred | No color | Occurred | Pink |
| *Staphylococcus simulans* NBRC109714 | Occurred | Pink | Occurred | Pink |
| *Staphylococcus haemolyticus* NBRC109768 | Occurred | No color | Occurred | Pink |
| *Staphylococcus warneri* NBRC109769 | Not occurred | — | Not occurred | — |
| *Staphylococcus hominis* ATCC700586 | Not occurred | — | Occurred | Pink |
| *Staphylococcus cohnii* subsp. *cohnii* NBRC109713 | Not occurred | — | Occurred | Pink |
| *Staphylococcus capitis* subsp. *captis* ATCC27840 | Not occurred | — | Not occurred | — |
| *Bacillus cereus* (Strain derived from medium powder) | Occurred | Pink | Occurred | Pink |
| *Bacillus licheniformis* NBRC12200 | Occurred | Pink | Occurred | Pink |
| *Bacillus subtilis* NBRC3134 | Not occurred | — | Not occurred | — |

As shown in Table 1, the microorganism culture sheet prepared with the use of the medium liquid containing the components of Experiment 1 contains only 6-chloro-3-indoxyl-α-D-glucoside that develops color in the presence of α-glucosidase as a color developer in the medium of the culture layer, but it does not contain colistin sodium methanesulfonate as a selection agent therein. For example, JP 2004-524041 A (Patent Literature 2) describes that *S. aureus* can be distinguished from other staphylococcal bacteria and detected with the use of a culture medium containing, as a color developer, an enzyme substrate that develops color in the presence of α-glucosidase.

When the microorganism culture sheet of Experiment 1 was used, as shown in Table 2, colonies formed by several staphylococcal bacteria other than *S. aureus* turned pink. Also, colonies formed by 2 bacterial species of *Bacillus* turned pink. The results demonstrate that the staphylococcal bacteria other than *S. aureus* and the bacteria of *Bacillus* may be detected as false-positive strains with the use of a microorganism culture sheet comprising a culture layer that contains, as a color developer, only 6-chloro-3-indoxyl-α-D-glucoside, but does not contain, as a selection agent, colistin sodium methanesulfonate.

Experiment 2: Test for Detecting Microorganisms Using a Medium Containing a Color Developer that Develops Color in the Presence of Phosphatase A test microbial sample was prepared in the same manner as in Experiment 1. With the use of a micropipette, 1 ml of the test microbial sample was inoculated into a culture layer of the microorganism culture sheet prepared with the use of the medium liquid containing the components shown in Table 1. In the same manner as with Experiment 1, the microorganism culture sheet into which the sample had been inoculated was subjected to incubation, and the color of the colony formed in the culture layer of the microorganism culture sheet and the color intensity were visually inspected. Each test microbial strain was subjected to the experiment described above. The names of the microbial strains to be tested used for the experiment and the conditions and the color of the colonies formed by the strains are shown in Table 3.

TABLE 3

| Strain | Culture for 24 hours | |
| --- | --- | --- |
| | Colony formation | Color |
| Staphylococcus aureus ATCC25923 | Occurred | Dark blue |
| Staphylococcus aureus NBRC100910 | Occurred | Dark blue |
| Staphylococcus aureus NBRC12732 | Occurred | Dark blue |
| Staphylococcus intermedius ATCC29663 | Occurred | Dark blue |
| Staphylococcus hyicus ATCC11249 | Occurred | Light blue |
| Staphylococcus epidermidis NBRC12993 | Occurred | Light blue |
| Staphylococcus saprophyticus subsp. saprophyticus NBRC102446 | Occurred | No color |
| Staphylococcus xylosus NBRC109770 | Occurred | Light blue |
| Staphylococcus sciuri ATCC29062 | Occurred | Light blue |
| Staphylococcus simulans NBRC109714 | Occurred | No color |
| Staphylococcus haemolyticus NBRC109768 | Occurred | No color |
| Staphylococcus warneri NBRC109769 | Not occurred | — |
| Staphylococcus hominis ATCC700586 | Not occurred | — |
| Staphylococcus cohnii subsp. cohnii NBRC109713 | Not occurred | — |
| Staphylococcus capitis subsp. captis ATCC27840 | Not occurred | — |
| Bacillus cereus (Strain derived from medium powder) | Occurred | Dark blue |
| Bacillus licheniformis NBRC12200 | Occurred | Dark blue |
| Bacillus subtilis NBRC3134 | Not occurred | — |

As shown in Table 1, the microorganism culture sheet prepared with the use of the medium liquid containing the components of Experiment 2 contains only 5-bromo-3-indoxyl phosphate that develops color in the presence of phosphatase as a color developer in the medium of the culture layer, but it does not contain colistin sodium methanesulfonate as a selection agent therein.

When the microorganism culture sheet of Experiment 2 was used, as shown in Table 3, colonies formed by several staphylococcal bacteria other than *S. aureus* turned dark blue to light blue. Also, colonies formed by 2 bacterial species of *Bacillus* turned dark blue. The results demonstrate that staphylococcal bacteria other than *S. aureus* and bacteria of *Bacillus* may be detected as false-positive strains with the use of a microorganism culture sheet comprising a culture layer that contains, as a color developer, only 5-bromo-3-indoxyl phosphate, but does not contain, as a selection agent, colistin sodium methanesulfonate.

Experiment 3: Test for Detecting Microorganisms Using a Medium Containing Two Types of Color Developers A test microbial sample was prepared in the same manner as in Experiment 1. With the use of a micropipette, 1 ml of the test microbial sample was inoculated into a culture layer of the microorganism culture sheet prepared with the use of the medium liquid containing the components shown in Table 1. In the same manner as with Experiment 1, the microorganism culture sheet into which the sample had been inoculated was subjected to incubation, and the color of the colony formed in the culture layer of the microorganism culture sheet and the color intensity were visually inspected. Each test microbial strain was subjected to the experiment described above. The names of the microbial strains to be tested used for the experiment and the conditions and the color of the colonies formed by the strains are shown in Table 4.

TABLE 4

| Strain | Culture for 24 hours | |
| --- | --- | --- |
| | Colony formation | Color |
| Staphylococcus aureus ATCC25923 | Occurred | Dark blue |
| Staphylococcus aureus NBRC100910 | Occurred | Dark blue |
| Staphylococcus aureus NBRC12732 | Occurred | Dark blue |
| Staphylococcus intermedius ATCC29663 | Occurred | Purple |
| Staphylococcus hyicus ATCC11249 | Occurred | Pink |
| Staphylococcus epidermidis NBRC12993 | Occurred | No color |
| Staphylococcus saprophyticus subsp. saprophyticus NBRC102446 | Occurred | Pink |
| Staphylococcus xylosus NBRC109770 | Occurred | No color |
| Staphylococcus sciuri ATCC29062 | Occurred | Light blue |
| Staphylococcus simulans NBRC109714 | Occurred | Pink |
| Staphylococcus haemolyticus NBRC109768 | Occurred | Pink |
| Staphylococcus warneri NBRC109769 | Not occurred | — |
| Staphylococcus hominis ATCC700586 | Not occurred | — |
| Staphylococcus cohnii subsp. cohnii NBRC109713 | Not occurred | — |
| Staphylococcus capitis subsp. captis ATCC27840 | Not occurred | — |
| Bacillus cereus (Strain derived from medium powder) | Occurred | Pink |
| Bacillus licheniformis NBRC12200 | Occurred | Pink |
| Bacillus subtilis NBRC3134 | Not occurred | — |

As shown in Table 1, the microorganism culture sheet prepared with the use of the medium liquid containing the components of Experiment 3 contains, as color developers, 6-chloro-3-indoxyl-α-D-glucoside that develops color in the presence of α-glucosidase and 5-bromo-3-indoxyl phosphate that develops color in the presence of phosphatase in the medium of the culture layer, but it does not contain colistin sodium methanesulfonate as a selection agent therein.

When *S. aureus* is present in the medium in the culture layer of the microorganism culture sheet of Experiment 3, the colony formed by such strain was deduced to turn, for example, purple, which is a mixed color of pink developed by α-glucosidase activity and blue to dark blue developed by phosphatase activity. When the microorganism culture sheet of Experiment 3 was used, however, the colony formed by *S. aureus* surprisingly turned dark blue, as shown in Table 4. In contrast, staphylococcal bacteria other than *S. intermedius* and *S. sciuri* did not form the colony, the colony formed thereby did not develop color, or the colony turned pink. The colony formed by *S. intermedius* turned purple. Such patterns of color development are deduced to occur since *S. intermedius* expresses both α-glucosidase and phosphatase. Accordingly, *S. aureus* can be specifically detected by identifying a sample that formed the dark blue colony as a positive strain, and also a sample that did not form the colony, a sample that formed the colony which did not develop color or a sample that formed the colony which turned pink as a negative strain. However, the colony of *S. sciuri* turned light blue. This indicates that such strain may be detected as a false-positive strain.

Experiment 4: Test for Detecting Microorganisms Using a Medium Containing Colistin Sodium Methanesulfonate A test microbial sample was prepared in the same manner as in Experiment 1. Also, the microorganism culture sheet was prepared in the same manner as in Experiment 1. The medium liquid used for preparing the microorganism culture sheet contains the solid components same as those used in Experiment 3 as shown in Table 1, a given amount of colistin sodium methanesulfonate at the final mass concentration as shown in Table 5, and a solvent for viscosity modification (methanol). With the use of a micropipette, 1 ml of the test microbial sample was inoculated into a culture layer of the microorganism culture sheet. In the same manner as with Experiment 1, the microorganism culture sheet into which the sample had been inoculated was subjected to incubation, culture was conducted for 24 hours, and the color of the colony formed in the culture layer of the microorganism culture sheet and the color intensity were visually inspected. Each test microbial strain was subjected to the experiment described above. The names of the microbial strains to be tested used for the experiment and the conditions of the colonies formed by the strains are shown in Table 5. In the table, a blank column indicates that a colony was formed under normal growth condition, and the term "Inhibited" indicates the condition under which the growth was inhibited. The colistin sodium methanesulfonate concentration indicated in the upper column is mass concentration (mg/cm$^3$) relative to the total volume of the dried culture layer before the sample was inoculated thereinto, and the concentration indicated in the lower column is mass concentration (mg/ml) relative to the total volume of the sample solution that was inoculated into the culture layer at the time of use.

TABLE 5

| Strain | Colistin sodium methanesulfonate (Upper column: mg/cm$^3$; Lower column: mg/ml) | | | | | | | | | |
|---|---|---|---|---|---|---|---|---|---|---|
| | 0 | 0.3 | 0.5 | 0.8 | 1.0 | 1.3 | 1.5 | 1.8 | 2.0 | 2.3 |
| | 0 | 0.1 | 0.2 | 0.3 | 0.4 | 0.5 | 0.6 | 0.7 | 0.8 | 0.9 |
| *Staphylococcus aureus* ATCC25923 | | | | | | | | | | |
| *Staphylococcus aureus* NBRC100910 | | | | | | | | | | |
| *Staphylococcus aureus* NBRC12732 | | | | | | | | | | |
| *Staphylococcus intermedius* ATCC29663 | | | | | | | | | | |
| *Staphylococcus saprophyticus* subsp. *saprophyticus* NBRC102446 | | Inhibited | Inhibited | Inhibited | Inhibited | Inhibited | Inhibited | Inhibited | Inhibited | Inhibited |
| *Staphylococcus xylosus* NBRC109770 | | | | | | | | | | Inhibited |
| *Staphylococcus sciuri* ATCC29062 | | | | | | | | | | Inhibited |
| *Staphylococcus carnosus* (Derived from coast beef) | | | | | Inhibited | Inhibited | Inhibited | Inhibited | Inhibited | |

| Strain | Colistin sodium methanesulfonate (Upper column: mg/cm$^3$; Lower column: mg/ml) | | | | | | |
|---|---|---|---|---|---|---|---|
| | 2.5 | 2.8 | 3.1 | 3.3 | 3.6 | 3.8 | 4.1 |
| | 1 | 1.1 | 1.2 | 1.3 | 1.4 | 1.5 | 1.6 |
| *Staphylococcus aureus* ATCC25923 | | | | | | | |
| *Staphylococcus aureus* NBRC100910 | | | | | | | |
| *Staphylococcus aureus* NBRC12732 | | | Inhibited | Inhibited | Inhibited | Inhibited | Inhibited |
| *Staphylococcus intermedius* ATCC29663 | | | | Inhibited | Inhibited | Inhibited | Inhibited |
| *Staphylococcus saprophyticus* subsp. *saprophyticus* NBRC102446 | Inhibited | Inhibited | Inhibited | Inhibited | Inhibited | Inhibited | Inhibited |
| *Staphylococcus xylosus* NBRC109770 | Inhibited | Inhibited | Inhibited | Inhibited | Inhibited | Inhibited | Inhibited |
| *Staphylococcus sciuri* ATCC29062 | Inhibited | Inhibited | Inhibited | Inhibited | Inhibited | Inhibited | Inhibited |
| *Staphylococcus carnosus* (Derived from coast beef) | Inhibited | Inhibited | Inhibited | Inhibited | Inhibited | Inhibited | Inhibited |

As shown in Tables 1 and 5, the microorganism culture sheet prepared with the use of the medium liquid containing the components of Experiment 4 contains, as color developers, 6-chloro-3-indoxyl-α-D-glucoside that develops color in the presence of α-glucosidase and 5-bromo-3-indoxyl phosphate that develops color in the presence of phosphatase and, as a selection agent, colistin sodium methanesulfonate at the concentration shown in Table 5 in the medium of the culture layer.

As shown in Table 5, colistin sodium methanesulfonate did not inhibit the growth of the S. aureus ATCC25923 strain and the NBRC100910 strain at the tested concentration of 0.3 to 4.1 mg/cm$^3$ (i.e., 0.1 to 1.6 mg/ml in the sample solution). Regarding the S. aureus NBRC12732 strain alone, the growth thereof was inhibited with the use of the microorganism culture sheet containing colistin sodium methanesulfonate at 3.1 mg/cm$^3$ (i.e., 1.2 mg/ml in the sample solution). In contrast, the growth of S. saprophyticus was inhibited with the use of the microorganism culture sheet containing colistin sodium methanesulfonate at 0.5 mg/cm$^3$ (i.e., 0.2 mg/ml in the sample solution) or more even though the strain was a Gram-positive bacterium. Also, the growth of S. xylosus and S. sciuri was inhibited with the use of the microorganism culture sheet containing colistin sodium methanesulfonate at 2.3 mg/cm$^3$ (i.e., 0.9 mg/ml in the sample solution) or more. The growth of S. carnosus was inhibited with the use of the microorganism culture sheet containing colistin sodium methanesulfonate at 1.3 mg/cm$^3$ (i.e., 0.5 mg/ml in the sample solution) or more. The results described above demonstrate that high-concentration colistin sodium methanesulfonate can be used as a selection agent exerting inhibitory effects on particular staphylococcal bacteria.

Experiment 5: Test for Detecting Microorganisms Using a Medium Containing Two Types of Color Developers and Colistin Sodium Methanesulfonate at High Concentration (1)

Figure 7:
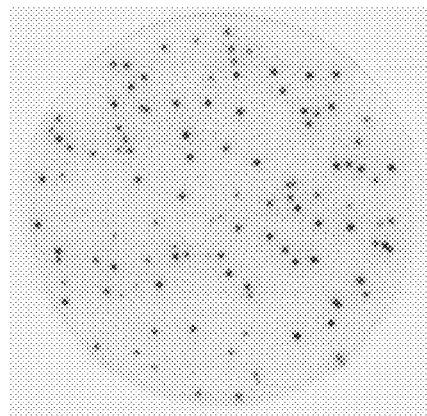
FIG. 7 shows photographs demonstrating the conditions of cell colony formation after the color development in Experiment 5 and the colors thereof; (a): the *S. aureus* ATCC25923 strain; (b): the *S. aureus* NBRC100910 strain; (c): the *S. aureus* NBRC12732 strain; (d): *S. intermedius*; (e): *S. hyicus*; and (f): *S. epidermidis*.
Figure 7:
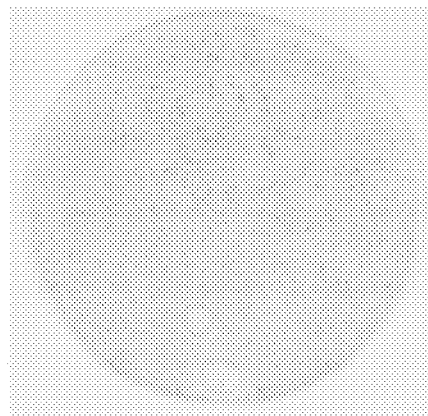
Figure 7:
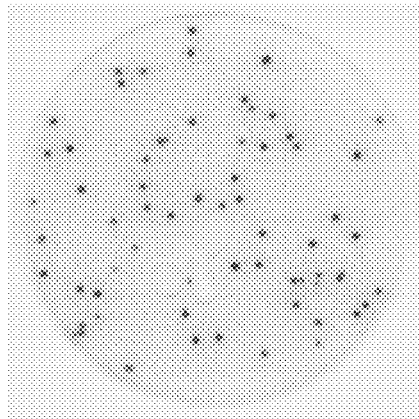
Figure 7:
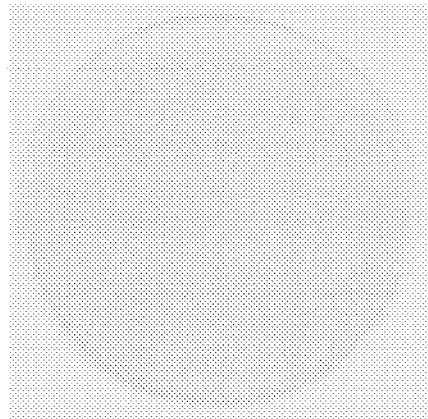
Figure 7:
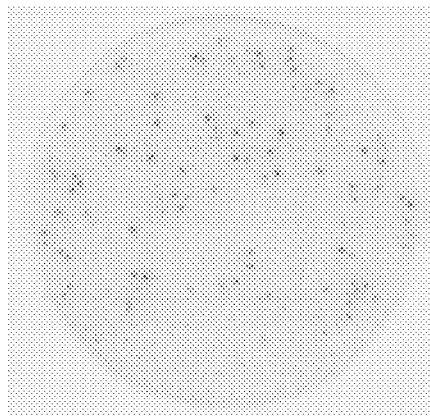
Figure 7:
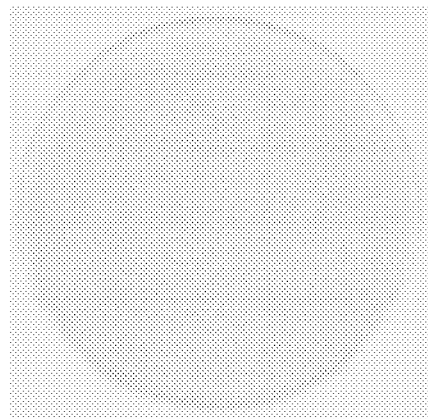
Figure 8:
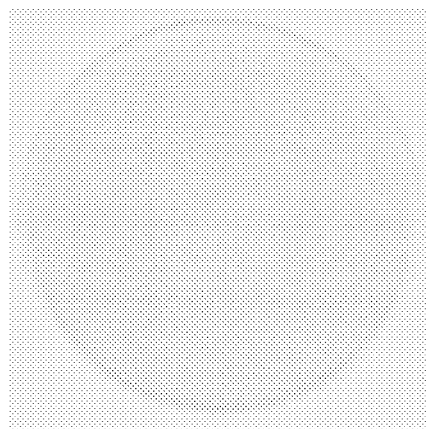
FIG. 8 shows photographs demonstrating the conditions of cell colony formation after the color development in Experiment 5 and the colors thereof; (a): *S. saprophyticus* subsp. *saprophyticus*; (b): *S. xylosus*; (c): *S. sciuri*; (d): *Bacillus cereus*; (e): *B. licheniformis*; and (f): *B. subtilis*.
Figure 8:
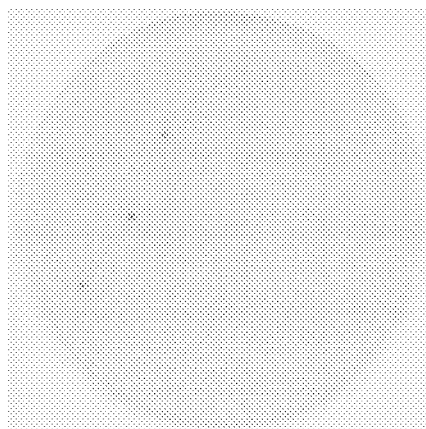
Figure 8:
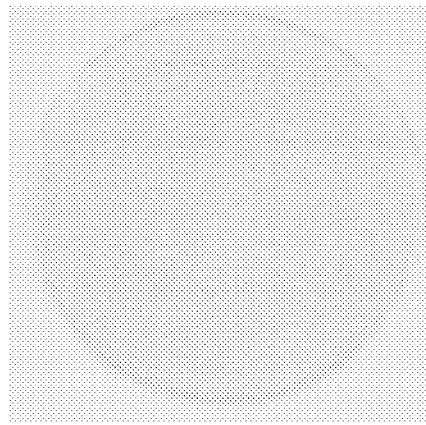
Figure 8:
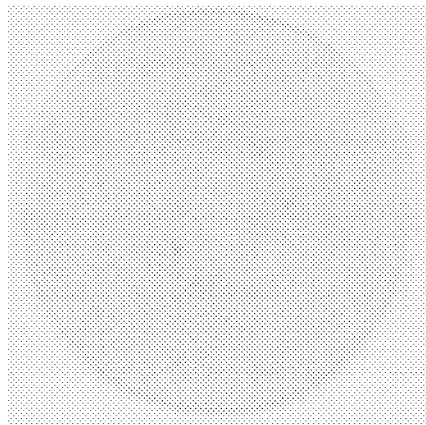
Figure 8:
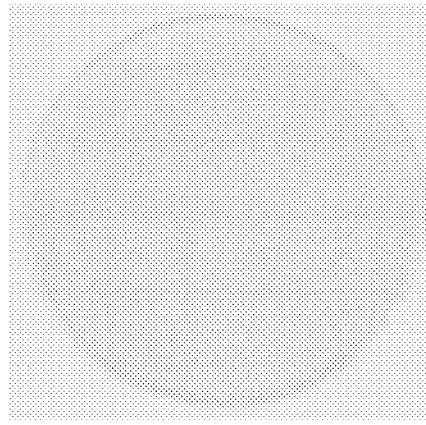
Figure 8:
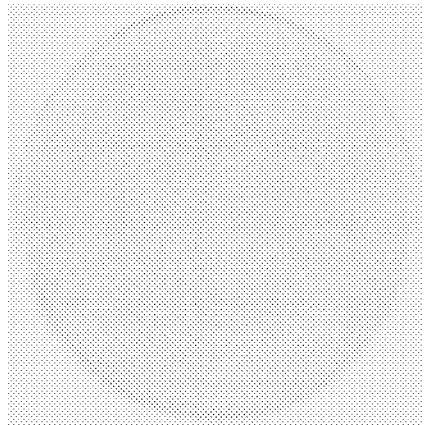

A test microbial sample was prepared in the same manner as in Experiment 1. Also, the microorganism culture sheet was prepared in the same manner as in Experiment 1. The medium liquid used for preparing the microorganism culture sheet contains the solid components same as those used in Experiment 3 as shown in Table 1, a given amount of colistin sodium methanesulfonate at the final mass concentration of 2.5 mg/cm$^3$ (i.e., 1 mg/ml in the sample solution), and a solvent for viscosity modification (methanol). With the use of a micropipette, 1 ml of the test microbial sample was inoculated into a culture layer of the microorganism culture sheet. In the same manner as with Experiment 1, the microorganism culture sheet into which the sample had been inoculated was subjected to incubation, and the color of the colony formed in the culture layer of the microorganism culture sheet and the color intensity were visually inspected. Each test microbial strain was subjected to the experiment described above. The names of the microbial strains to be tested used for the experiment and the conditions and the color of the colonies formed by the strains are shown in Table 6. FIG. 7 and FIG. 8 show the conditions of colony formation of each strain after color development and the color thereof. In the figures, FIG. 7(a) shows the S. aureus ATCC25923 strain, FIG. 7(b) shows the S. aureus NBRC100910 strain, FIG. 7(c) shows the S. aureus NBRC12732 strain, FIG. 7(d) shows S. intermedius, FIG. 7(e) shows S. hyicus, and FIG. 7(f) shows S. epidermidis. FIG. 8(a) shows S. saprophyticus subsp. saprophyticus, FIG. 8(b) shows S. xylosus, FIG. 8(c) shows S. sciuri, FIG. 8(d) shows Bacillus cereus, FIG. 8(e) shows Bacillus licheniformis, and FIG. 8(f) shows Bacillus subtilis.

TABLE 6

| | Culture for 24 hours | |
|---|---|---|
| Strain | Colony formation | Color |
| Staphylococcus aureus ATCC25923 | Occurred | Dark blue |
| Staphylococcus aureus NBRC100910 | Occurred | Dark blue |
| Staphylococcus aureus NBRC12732 | Occurred | Dark blue |
| Staphylococcus intermedius ATCC29663 | Occurred | Purple |
| Staphylococcus hyicus ATCC11249 | Not occurred | — |
| Staphylococcus epidermidis NBRC12993 | Not occurred | — |
| Staphylococcus saprophyticus subsp. saprophyticus NBRC102446 | Not occurred | — |
| Staphylococcus xylosus NBRC109770 | Not occurred | — |
| Staphylococcus sciuri ATCC29062 | Not occurred | — |
| Staphylococcus simulans NBRC109714 | Not occurred | — |
| Staphylococcus haemolyticus NBRC109768 | Not occurred | — |
| Staphylococcus warneri NBRC109769 | Not occurred | — |
| Staphylococcus hominis ATCC700586 | Not occurred | — |
| Staphylococcus cohnii subsp. cohnii NBRC109713 | Not occurred | — |
| Staphylococcus capitis subsp. captis ATCC27840 | Not occurred | — |
| Bacillus cereus (Strain derived from medium powder) | Occurred | Pink |
| Bacillus licheniformis NBRC12200 | Occurred | Pink |
| Bacillus subtilis NBRC3134 | Not occurred | — |

When the microorganism culture sheet of Experiment 5 was used, as shown in Table 6, the colony of S. aureus turned dark blue as with the case of Experiment 3 (FIG. 7(a) to (c)). In contrast, staphylococcal bacteria other than S. intermedius did not form the colony. In particular, the growth of S. sciuri, the colony formation of which was confirmed in Experiments 1 to 3, was inhibited with the use of the microorganism culture sheet containing colistin sodium methanesulfonate at 2.5 mg/cm$^3$ (i.e., 1 mg/ml in the sample solution), and the colony was not formed. The colony of S. intermedius turned purple (FIG. 7(d)). The colonies of two types of bacteria of Bacillus turned pink (FIGS. 8(d) and (e)). Accordingly, it was found that S. aureus could be specifically detected without detecting a false-positive strain even in the presence of other staphylococcal bacteria and Bacillus bacteria in the sample by identifying a sample that formed the dark blue colony as a positive strain, and also a sample that did not form the colony or a sample that formed the colony which turned purple or pink as a negative strain.

Experiment 6: Test for Detecting Microorganisms Using a Medium Containing Two Types of Color Developers and Colistin Sodium Methanesulfonate at High Concentration (2)

Figure 9:
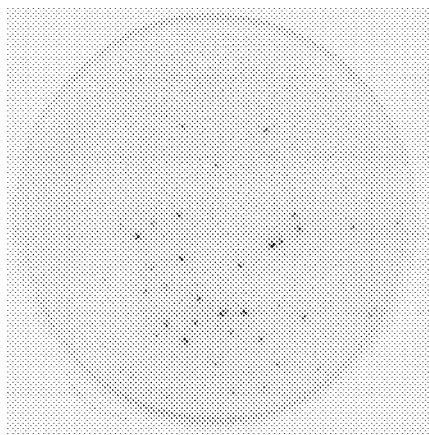
FIG. 9 shows photographs demonstrating the conditions of cell colony formation after the color development in Experiment 6 and the colors thereof; (a): the *S. aureus* ATCC25923 strain; (b): the *S. aureus* NBRC100910 strain; (c): the *S. aureus* NBRC12732 strain; (d): *S. intermedius*; (e): *S. hyicus*; and (f): *S. epidermidis*.
Figure 9:
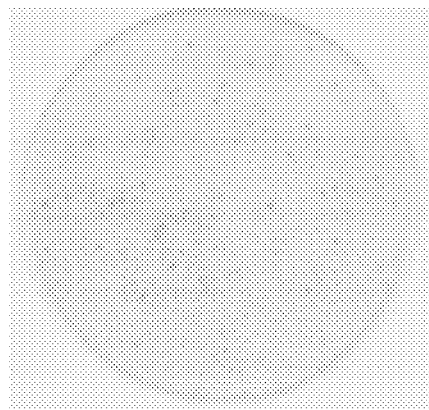
Figure 9:
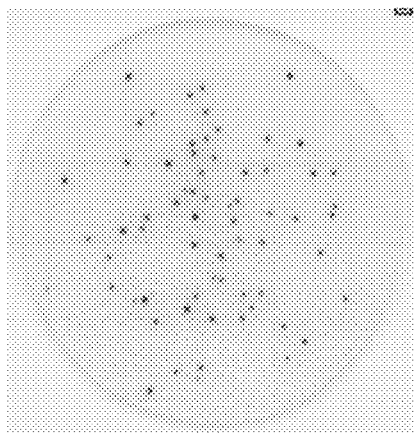
Figure 9:
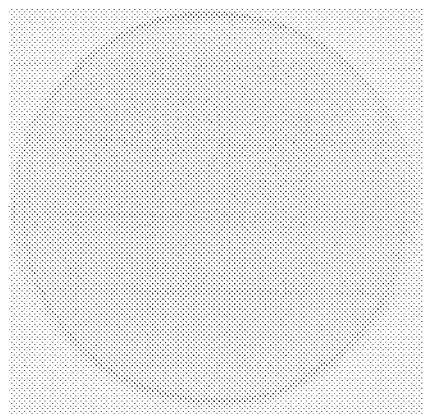
Figure 9:
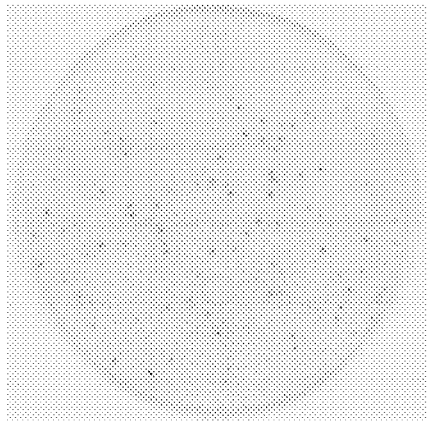
Figure 9:
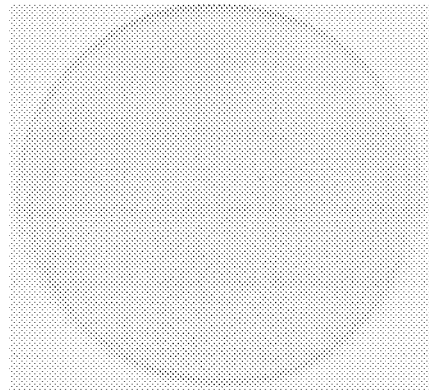
Figure 10:
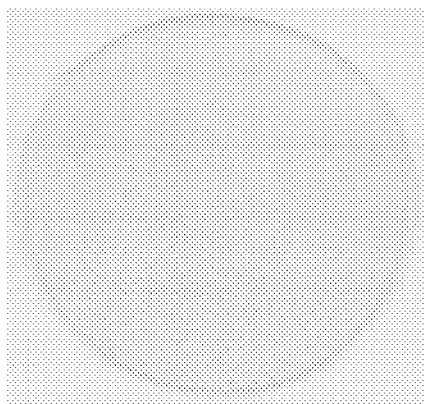
FIG. 10 shows photographs demonstrating the conditions of cell colony formation after the color development in Experiment 6 and the colors thereof; (a): *S. saprophyticus* subsp. *saprophyticus*; (b): *S. xylosus*; (c): *S. sciuri*; (d): *S. simulans*; (e): *S. haemolyticus*; and (f): *S. warneri*.
Figure 10:
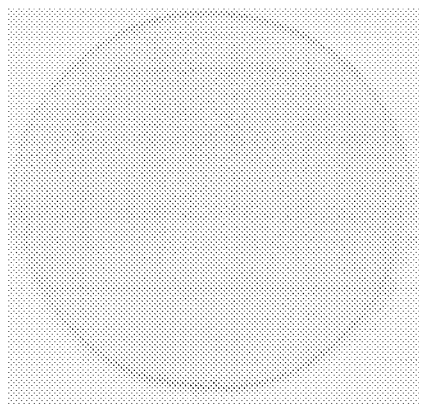
Figure 10:
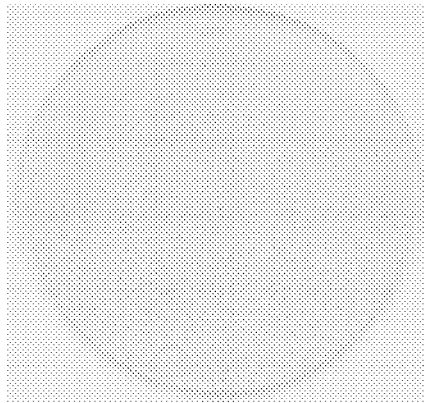
Figure 10:
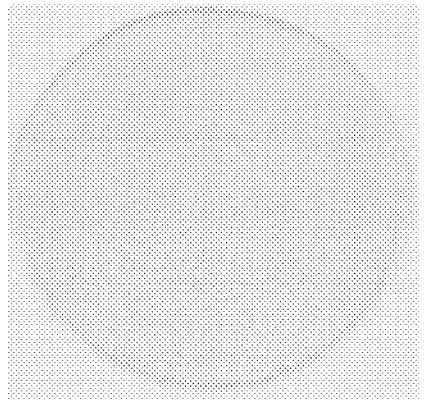
Figure 10:
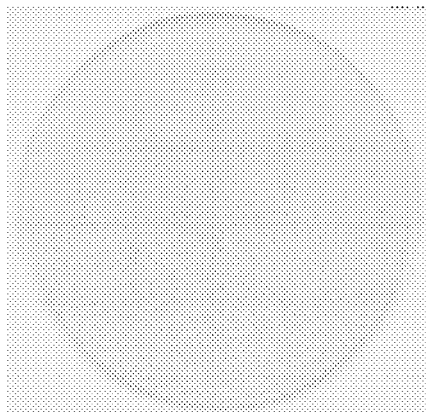
Figure 10:
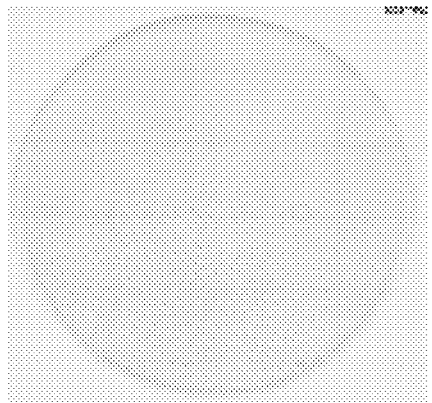
Figure 11:
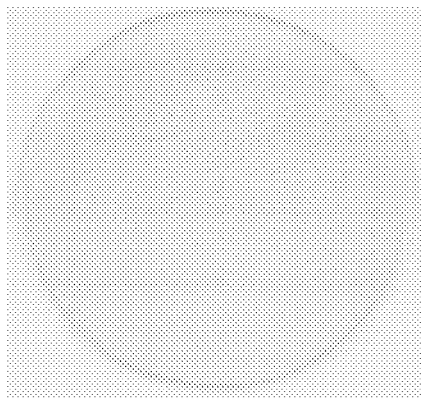
FIG. 11 shows photographs demonstrating the conditions of cell colony formation after the color development in Experiment 6 and the colors thereof; (a): *S. hominis*; (b): *S. cohnii*; (c): *S. capitis*; (d): *B. cereus*; (e): *B. licheniformis*; and (f): *B. subtilis*.
Figure 11:
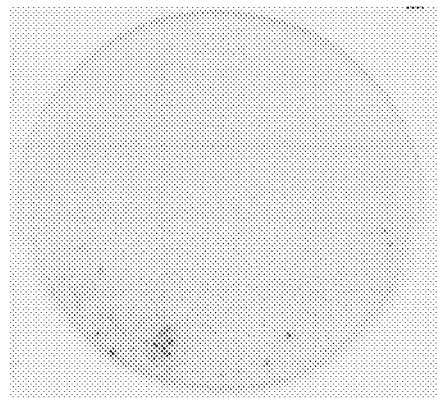
Figure 11:
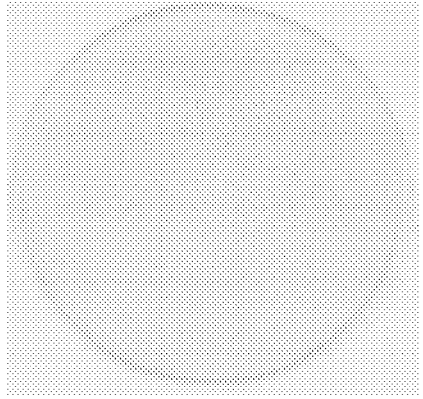
Figure 11:
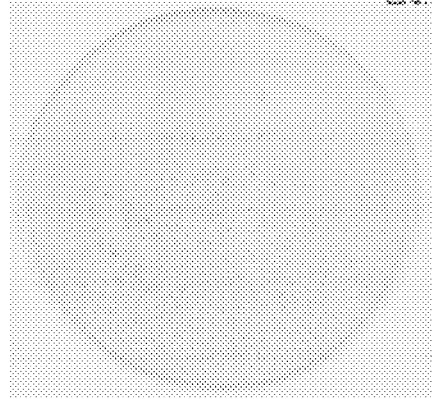
Figure 11:
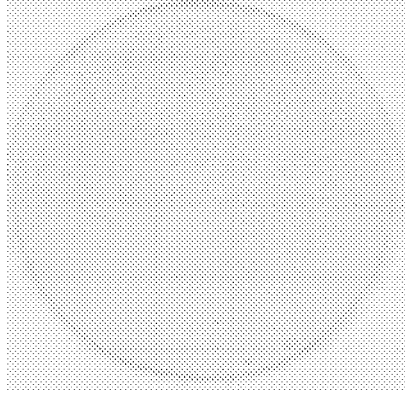
Figure 11:
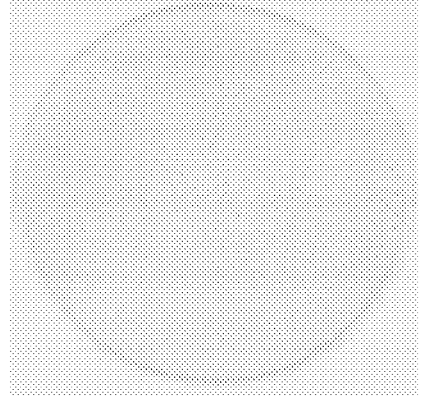

A test microbial sample was prepared in the same manner as in Experiment 1. Also, the microorganism culture sheet was prepared in the same manner as in Experiment 1. The medium liquid used for preparing the microorganism culture sheet contains solid components prepared by replacing the color developer that develops color in the presence of α-glucosidase and the color developer that develops color in the presence of phosphatase in the solid components used in Experiment 3 as shown in Table 1 by 5-bromo-4-chloro-3-indoxyl-α-D-glucoside and 5-bromo-6-chloro-3-indoxyl phosphate, respectively. In addition, the medium liquid contains a given amount of colistin sodium methanesulfonate at the final mass concentration of 2.5 mg/cm$^3$ (i.e., 1 mg/ml in the sample solution) and a solvent for viscosity modification (methanol). With the use of a micropipette, 1 ml of the test microbial sample was inoculated into a culture layer of the microorganism culture sheet. In the same manner as with Experiment 1, the microorganism culture sheet into which the sample had been inoculated was subjected to incubation, and the color of the colony formed in the culture layer of the microorganism culture sheet and the color intensity were visually inspected. Each test microbial strain was subjected to the experiment described above. The names of the microbial strains to be tested used for the experiment and the conditions and the color of the colonies formed by the strains are shown in Table 7. FIG. 9 to FIG. 11 show the conditions of colony formation of each strain after color development and the color thereof. In the figures, FIG. 9(a) shows the S. aureus ATCC25923 strain, FIG. 9(b) shows the S. aureus NBRC100910 strain, FIG. 9(c) shows the S. aureus NBRC12732 strain, FIG. 9(d) shows S. intermedius, FIG. 9(e) shows S. hyicus, and FIG. 9(f) shows S. epidermidis, respectively. FIG. 10(a) shows S. saprophyticus subsp. saprophyticus, FIG. 10(b) shows S. xylosus, FIG. 10(c) shows S. sciuri, FIG. 10(d) shows S. simulans, FIG. 10(e) shows S. haemolyticus, and FIG. 10(f) shows S. warneri. FIG. 11(a) shows S. hominis, FIG. 11(b) shows S. cohnii, FIG. 11(c) shows S. capitis, FIG. 11(d) shows Bacillus cereus, FIG. 11(e) shows Bacillus licheniformis, and FIG. 11(f) shows Bacillus subtilis, respectively.

TABLE 7

| | Culture for 24 hours | |
|---|---|---|
| Strain | Colony formation | Color |
| Staphylococcus aureus ATCC25923 | Occurred | Magenta |
| Staphylococcus aureus NBRC100910 | Occurred | Magenta |
| Staphylococcus aureus NBRC12732 | Occurred | Magenta |
| Staphylococcus intermedius ATCC29663 | Occurred | Gray |
| Staphylococcus hyicus ATCC11249 | Not occurred | — |
| Staphylococcus epidermidis NBRC12993 | Not occurred | — |
| Staphylococcus saprophyticus subsp. saprophyticus NBRC102446 | Not occurred | — |
| Staphylococcus xylosus NBRC109770 | Not occurred | — |
| Staphylococcus sciuri ATCC29062 | Not occurred | — |
| Staphylococcus simulans NBRC109714 | Not occurred | — |
| Staphylococcus haemolyticus NBRC109768 | Not occurred | — |
| Staphylococcus warneri NBRC109769 | Not occurred | — |
| Staphylococcus hominis ATCC700586 | Not occurred | — |
| Staphylococcus cohnii subsp. cohnii NBRC109713 | Not occurred | — |
| Staphylococcus capitis subsp. captis ATCC27840 | Not occurred | — |
| Bacillus cereus (Strain derived from medium powder) | Occurred | Blue |
| Bacillus licheniformis NBRC12200 | Occurred | Gray |
| Bacillus subtilis NBRC3134 | Not occurred | — |

When the microorganism culture sheet of Experiment 6 was used, as shown in Table 7, the colony of S. aureus turned magenta (FIG. 9(a) to (c)). In contrast, staphylococcal bacteria other than S. intermedius did not form the colony. In particular, the growth of S. sciuri, the colony formation of which had been confirmed in Experiments 1 to 3, was inhibited with the use of the microorganism culture sheet containing colistin sodium methanesulfonate at 2.5 mg/cm$^3$ (i.e., 1 mg/ml in the sample solution), and the colony was not formed. The colony of S. intermedius turned gray (FIG. 9(d)). The colonies of two types of bacteria of Bacillus turned blue or gray (FIGS. 11(d) and (e)). Accordingly, it was found that S. aureus could be specifically detected without detecting a false-positive strain even in the presence of other staphylococcal bacteria and Bacillus bacteria in the sample by identifying a sample that formed the magenta colony as a positive strain, and also a sample that did not form the colony or a sample that formed the colony which turned gray or blue as a negative strain.

This description includes part or all of the content as disclosed in the description and/or drawings of Japanese Patent Application Nos. 2016-016378 and 2016-113278, which are priority documents of the present application.

All publications, patents, and patent applications cited herein are incorporated herein by reference in their entirety.

DESCRIPTION OF NUMERAL REFERENCES

10: Substrate sheet
20: Frame layer
25: Fixing member
30: Culture layer
40: Cover sheet

The invention claimed is:

1. A microorganism culture substrate for detecting Staphylococcus aureus comprising: a substrate and a culture layer provided on an upper surface of the substrate, wherein the culture layer comprises a medium comprising one or more nutrient components, a color developer that develops color in the presence of α-glucosidase, a color developer that develops color in the presence of phosphatase, and colistin sodium methanesulfonate at 0.5 mg/cm$^3$ or more.

2. The microorganism culture substrate according to claim 1, which further comprises a cover sheet to cover the other side of the culture layer that is not covered by the substrate, wherein the substrate is a sheet, and wherein the culture layer further comprises polyvinylpyrrolidone and one or more gelling agents.

3. A method for detecting *Staphylococcus aureus* comprising:
adding a microorganism-containing sample to the culture layer of the microorganism culture substrate according to claim 1;
incubating the microorganism culture substrate with the added sample; and
identifying the presence of *Staphylococcus aureus* based on the growth of colored colony or colonies in the culture layer, wherein the colony or colonies are colored by at least one color developer in the culture layer.

4. The method according to claim 3, wherein the microorganism-containing sample is a liquid, and the colistin sodium methanesulfonate is 0.2 mg/ml or more after the sample is added to the culture layer.

5. A method for detecting *Staphylococcus aureus* comprising:
adding a microorganism-containing sample to a medium comprising one or more nutrient components, a color developer that develops color in the presence of α-glucosidase, a color developer that develops color in the presence of phosphatase, and colistin sodium methanesulfonate at 0.5 mg/cm$^3$ or more;
incubating the medium with the added sample; and
identifying the presence of *Staphylococcus aureus* based on the growth of colored colony or colonies in the medium, wherein the colony or colonies are colored by at least one color developer in the medium.

6. The microorganism culture substrate according to claim 1, wherein the color developer that develops color in the presence of α-glucosidase is 6-chloro-3-indoxyl-α-D-glucoside, and the color developer that develops color in the presence of phosphatase is 5-bromo-3-indoxyl phosphate.

7. The microorganism culture substrate according to claim 1, wherein the color developer that develops color in the presence of α-glucosidase is 5-bromo-4-chloro-3-indoxyl-α-D-glucoside, and the color developer that develops color in the presence of phosphatase is 5-bromo-6-chloro-3-indoxyl phosphate.

8. The microorganism culture substrate according to claim 1, wherein the colistin sodium methanesulfonate is 0.5 to 4.1 mg/cm$^3$.

9. The microorganism culture substrate according to claim 8, wherein the colistin sodium methanesulfonate is 0.5 to 2.8 mg/cm$^3$.

10. The microorganism culture substrate according to claim 9, wherein the colistin sodium methanesulfonate is 2.3 to 2.8 mg/cm$^3$.

11. The method according to claim 5, wherein the color developer that develops color in the presence of α-glucosidase is 6-chloro-3-indoxyl-α-D-glucoside, and the color developer that develops color in the presence of phosphatase is 5-bromo-3-indoxyl phosphate.

12. The method according to claim 5, wherein the color developer that develops color in the presence of α-glucosidase is 5-bromo-4-chloro-3-indoxyl-α-D-glucoside, and the color developer that develops color in the presence of phosphatase is 5-bromo-6-chloro-3-indoxyl phosphate.

13. The method according to claim 5, wherein the colistin sodium methanesulfonate is 0.5 to 4.1 mg/cm$^3$.

14. The method according to claim 13, wherein the colistin sodium methanesulfonate is 0.5 to 2.8 mg/cm$^3$.

15. The method according to claim 14, wherein the colistin sodium methanesulfonate is 2.3 to 2.8 mg/cm$^3$.

* * * * *